(12) United States Patent
Hansson

(10) Patent No.: US 8,609,605 B2
(45) Date of Patent: Dec. 17, 2013

(54) IMMUNOMODULATORY METHODS FOR TREATMENT OF ATHEROSCLEROSIS VIA INHIBITION OF CD4+ T CELL RESPONSE TO APOB100

(75) Inventor: Goran Hansson, Stockholm (SE)

(73) Assignee: CardioVax, LLC, Torrance, CA (US)

( * ) Notice: Subject to any disclaimer, the term of this patent is extended or adjusted under 35 U.S.C. 154(b) by 0 days.

(21) Appl. No.: 13/257,045

(22) PCT Filed: Mar. 17, 2010

(86) PCT No.: PCT/SE2010/050299
§ 371 (c)(1),
(2), (4) Date: Feb. 29, 2012

(87) PCT Pub. No.: WO2010/107380
PCT Pub. Date: Sep. 23, 2010

(65) Prior Publication Data
US 2012/0148605 A1    Jun. 14, 2012

(30) Foreign Application Priority Data

Mar. 17, 2009   (SE) ..................................... 0950161

(51) Int. Cl.
| A61P 9/10 | (2006.01) |
| A61K 39/00 | (2006.01) |
| A61K 39/395 | (2006.01) |
| C07K 16/28 | (2006.01) |
| C07K 14/725 | (2006.01) |
| A61K 38/16 | (2006.01) |

(52) U.S. Cl.
USPC ...... 514/1.9; 424/185.1; 424/154.1; 530/350; 530/388.75

(58) Field of Classification Search
None
See application file for complete search history.

(56) References Cited

U.S. PATENT DOCUMENTS

| 5,223,426 | A | 6/1993 | Skibbens et al. |
| 5,766,947 | A | 6/1998 | Rittershaus et al. |
| 7,371,385 | B2 * | 5/2008 | Offner .................. 424/184.1 |
| 2002/0150891 | A1 | 10/2002 | Hood et al. |
| 2003/0165819 | A1 | 9/2003 | McGowan et al. |
| 2004/0002111 | A1 | 1/2004 | Hansson et al. |
| 2005/0152900 | A1 | 7/2005 | Najib et al. |
| 2005/0260222 | A1 | 11/2005 | Gupta et al. |
| 2006/0014941 | A1 * | 1/2006 | Rosloniec ................ 536/23.5 |
| 2006/0018929 | A1 | 1/2006 | Zaia et al. |
| 2009/0208538 | A1 | 8/2009 | Darnell |

FOREIGN PATENT DOCUMENTS

| WO | WO-9405801 A1 | 3/1994 |
| WO | 99/031227 A2 | 6/1999 |
| WO | 01/023414 A2 | 4/2001 |
| WO | WO-2004030698 A1 | 4/2004 |
| WO | 2007/116409 A2 | 10/2007 |
| WO | 2008/055354 A1 | 5/2008 |
| WO | 2010/107380 A1 | 9/2010 |
| WO | 2012/038922 A1 | 3/2012 |

OTHER PUBLICATIONS

Hermansson et al (2010. J Exp Med. 207(5): 1081-1093).*
Phillips, 2001. J Pharm Pharmacology 53: 1169-1174.*
International Search Report for International Application No. PCT/SE2010/050299 filed Mar. 17, 2010.
Chyu et al., "Choking off plaque neovascularity: a promising atheroprotective strategy or a double edged sword?" Arteriosclerosis, Thrombosis, and Vascular Biology, May 2007, vol. 27(5), pp. 993-995.
Fredrickson et al., "Identification of immune responses against aldehyde-modified peptide sequences in apoB associated with cardiovascular disease." Arteriosclerosis Thrombosis and Vascular Biology, vol. 23(5), May 2003, pp. 872-878.
Fredrickson et al.,"Inhibition of atherosclerosis in apoE-null mice by immunization with apoB-100 peptide sequences." Arteriosclerosis, Thrombosis, Vascular Biology, Highwire Press, Philadelphia, PA, US, vol. 23(5), May 1, 2003, pp. 879-884.
Herbin et al.,"Continuous subcutaneous delivery of apolipoprotein B-derived peptides induces T cells anergyand reduces the progression of established atheroscelorsis in mice." Circulation, vol. 116(16), Suppl. S., Oct. 2007, p. 145.
Li et al., "Effects of rapamycin-treated HSP60-pulsed dendritic cells on progression of atherosclerotic plaque in mice." Zhongguo Bingli Shengli Zazhi (2006), 22(6), 1079-1082, Peop. Rep. China.
Nilsson et al., "Vaccines modulating lipoprotein autoimmunity as a possible future therapy for cardiovascular disease." Journal of Internal Medicine, vol. 266(3), Jun. 25, 2009, pp. 221-231.
Yang et al., "Generation of HSP60-specific regulatory T cell and effect on atherosclerosis." Cellular Immunology, vol. 243, 2006, pgs. 90-95.
Zhao et al., "Athero-protective Effects of Immunization with apo-B 100 Related Peptide Vaccine in apoE-/- Mice is Associated with Enhanced CD8 Regulatory T Cell Response." Circulation, vol. 120(18), Suppl. 2., Nov. 3, 2009, p. S1018.
International Preliminary Report and Written Opnion dated Sep. 29, 2011 issued in corresponding International Application No. PCT/SE2010/050299.
Chyu Ky et al. "Immunization using an ApoB100 related epitope reduces atherosclerosis and plaque inflammation in hypercholesterolemic apo E (-/-) mice." Biochem. Biophys. Res. Commun. 338:1982-1989, 2005.
Ren et al., Progress of the Study of Vaccine for Atherosclerosis. Chin. J. Biologicals, vol. 18, No. 2 (2005).
International Search Report for International Application No. PCT/IB2011/054178 filed Sep. 22, 2011.

* cited by examiner

*Primary Examiner* — Zachary Howard
(74) *Attorney, Agent, or Firm* — K&L Gates LLP; Louis C. Cullman; Jennifer Rosenfield

(57) ABSTRACT

Immunostimulatory methods and systems for treating or preventing atherosclerosis and/or a condition associated thereto in an individual.

9 Claims, 11 Drawing Sheets

IMMUNOMODULATORY METHODS FOR TREATMENT OF ATHEROSCLEROSIS VIA INHIBITION OF CD4+ T CELL RESPONSE TO APOB100

CROSS REFERENCE TO RELATED APPLICATIONS

This application claims priority to the Swedish patent application No. 0950161-0, filed on Mar. 17, 2009 entitled "Abrogation of T cell Response to Low Density Lipoprotein as a Treatment for Atherosclerosis", which is incorporated herein by reference in its entirety.

TECHNICAL FIELD

The present disclosure relates to immunomodulatory methods and systems that are particularly suitable for treatment and/or prevention of atherosclerosis and/or conditions associated thereto and related proteins, peptides and compositions.

BACKGROUND

Atherosclerosis is currently viewed as a chronic lipid-related and immunemediated inflammatory disease of the arterial walls. Many immune components have been identified that participate in atherogenesis and pre-clinical studies have yielded promising results suggesting that immune-modulatory therapies targeting these components can reduce atherosclerosis.

SUMMARY

Provided herein, are methods and systems for inducing immunomodulatory responses in an individual. In several embodiments, the immunomodulatory responses induced by the methods and systems of the present disclosure are associated to a therapeutic or preventive effect related to atherosclerosis in the individual or a condition associated thereto.

According to a first aspect, a method and system to treat and/or prevent atherosclerosis in an individual is described. The method comprises: inhibiting in the individual a CD4+ T cell response to ApoB100, in particular by administering a therapeutically effective amount of a compound capable of inhibiting said response. The system comprises one or more agents suitable to inhibit CD4+ T cell response to ApoB100 of the individual and one or more agents suitable to detect the reduced response in the individual.

According to a second aspect, a method and system to treat and/or prevent atherosclerosis in an individual is described. The method comprises: inhibiting in the individual T cell receptor beta variable 31 (TCR TRBV31), in particular by administering a therapeutically effective amount of a compound capable of inhibiting said receptor. The system comprises one or more agents suitable to inhibit T cell receptor beta variable 31 of the individual and one or more agents suitable to detect the inhibition in the individual. Alternatively, the method comprises: inhibiting in individual a T cell receptor with a DNA sequence highly homologous to that of TRBV31, in particular by administering a therapeutically effective amount of a compound capable of inhibiting said receptor. The system comprises one or more agents suitable to inhibit such T cell receptor of the individual and one or more agents suitable to detect the inhibition in the individual.

According to a third aspect, a method and system to treat and/or prevent atherosclerosis in an individual is described. The method comprises: immunizing the individual against T cell receptor beta variable 31, for example by administering TCR TRBV31 peptide SEQ ID NO: 1 or other TCR TRBV31 immunogenic fragments in particular from CDR2 variable region. The system comprises one or more agents suitable to immunize the individual against T cell receptor beta variable 31 of the individual and one or more agents suitable to detect the immunization in the individual. Alternatively, the method comprises: immunizing the individual against a T cell receptor highly homologous to TRBV31, for example by administering the homologous (human) TCR TRBV30 or a TCR TRBV30 immunogenic fragment in particular from CDR2 variable region. The system then comprises one or more agents suitable to immunize the individual against such a T cell receptor of the individual and one or more agents suitable to detect the immunization in the individual.

According to a fourth aspect, a T cell receptor beta variable 31 or an immunogenic fragment thereof is described, the T cell receptor beta variable 31, for use as a medicament.

According to a fifth aspect, T cell receptor beta variable 31 or an immunogenic fragment thereof is described, the T cell receptor beta variable 31, for use in the treatment of atherosclerosis.

According to a sixth aspect, a T cell receptor highly homologous to that of TRBV31, such as the homologous human TCR TRBV30 or a TCR TRBV30 immunogenic fragment in particular from CDR2 variable region, is used in the treatment of atheroscleros.

According to a seventh aspect, an antibody reactive to the T cell receptor beta variable 31 (TCR TRBV31) or an immunogenic fragment thereof for use as a medicament.

According to an eighth aspect, an antibody reactive to a T cell receptor highly homologous to that of TRBV31, such as the homologous human TCR TRBV30 or a TCR TRBV30 immunogenic fragment in particular from CDR2 variable region for use as a medicament.

According to a ninth aspect, an antibody reactive to the T cell receptor beta variable 31 (TCR TRBV31) or an immunogenic fragment thereof for use in the treatment of atherosclerosis.

According to a tenth eleventh aspect, an antibody reactive to a T cell receptor highly homologous to that of TRBV31, such as the homologous human TCR TRBV30 or a TCR TRBV30 immunogenic fragment in particular from CDR2 variable region for use in the treatment of atherosclerosis.

According to a eleventh aspect, a composition and in particular, a vaccine is described, the composition comprising at least one of the T cell receptor beta variable 31 (TCR TRBV31), an immunogenic fragment thereof or an antibody together with an adjuvant and/or excipient. In several embodiments the adjuvant and/or excipients are pharmaceutically acceptable and the composition is pharmaceutical composition.

According to a twelfth aspect, a composition and in particular, a vaccine is described, the composition comprising at least one of the T cell receptor beta variable 31 (TCR TRBV31), an immunogenic fragment thereof or an antibody together with an adjuvant and/or excipient. In several embodiments the adjuvant and/or excipients are pharmaceutically acceptable and the composition is pharmaceutical composition.

According to a thirteenth aspect, a hybridoma from mice immunized with oxLDL and carrying human ApoB100 as a transgene (huB100t9) is described and in particular the hybridoma clone 48-5 deposited according to the Budapest Treaty with the DSMZ-Deutsche Sammlung von Mikro-organismen und Zellkulturen GmbH, Inhofftenstrasse 7 B, 38124 Braunschweig, Germany, on Jan. 22, 2009 with the accession number DSM ACC2986.

According to a fourteenth aspect, the hybridoma clone 48-5 deposited according to the Budapest Treaty with the DSMZ-Deutsche Sammlung von Mikro-organismen und Zellkulturen GmbH, Inhofftenstrasse 7 B, 38124 Braunschweig, Germany, on Jan. 22, 2009 with the accession number DSM ACC2986 is used to identify a compound inhibiting a CD4+ T cell response to ApoB100. The compound is identified by its capacity to prevent activation of 48-5 upon exposure to apoB100 or a fragment thereof.

The methods and systems herein described can be used in connection with applications wherein inhibition of CD4+ T cell response to ApoB100, inhibition of CD4 +TRBV31 binding to ApoB100, and/or a therapeutic or preventive effect for atherosclerosis in an individual is described.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION OF PREFERRED EMBODIMENTS

Figure 1:
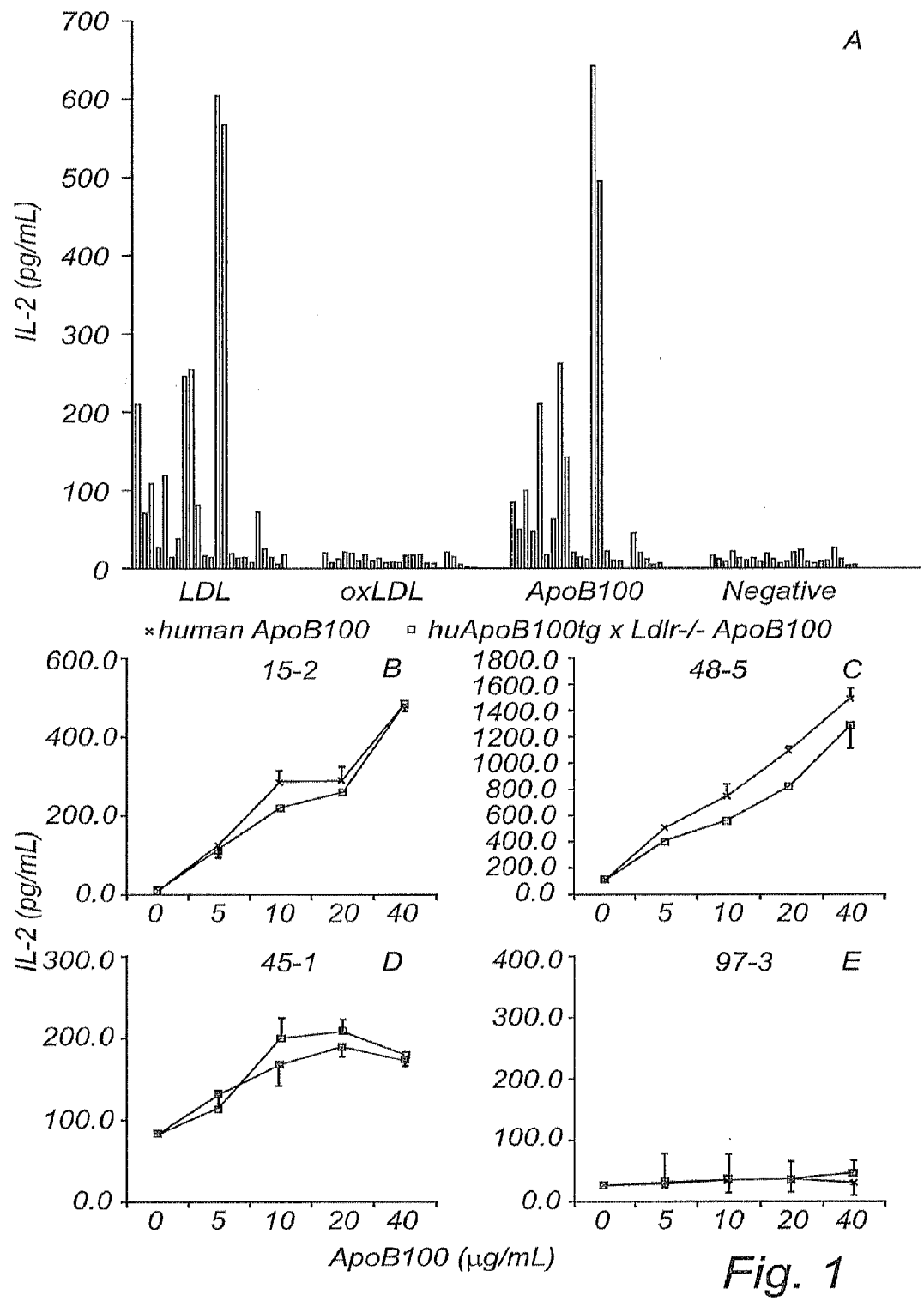
FIGS. 1A-1E show diagrams illustrating results related to T cell recognition of native LDL and ApoB100 according to an embodiment herein described.

Provided herein are methods and systems and related products and compositions for treating and/or preventing atherosclerosis or a condition associated thereto in individuals.

The term "treating" or "treatment" as used herein indicates any activity that is part of a medical care for, or that deals with, a condition medically or surgically. The term "preventing" or "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates as usually the physical status of the body of an individual (as a whole or of one or more of its parts) that does not conform to a physical status of the individual (as a whole or of one or more of its parts) that is associated with a state of complete physical, mental and possibly social well-being. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The wording "associated to" as used herein with reference to two items indicates a relation between the two items such that the occurrence of a first item is accompanied by the occurrence of the second item, which includes but is not limited to a cause-effect relation and sign/symptoms-disease relation.

The term "individuals" as used herein indicates a single biological organism such as higher animals and in particular vertebrates such as mammals and more particularly human beings.

Atherosclerosis is currently viewed as a chronic lipid-related and immunemediated inflammatory disease of the arterial walls. Many immune components have been identified that participate in atherogenesis and pre-clinical studies have yielded promising results suggesting that immunomodulatory therapies targeting these components can reduce atherosclerosis.

The term "atherosclerosis" as used herein indicates a cardiovascular condition, and in particular a chronic inflammatory disease characterized by the accumulation of lipoproteins eliciting an inflammatory response in the intima of the arterial wall. The tunica intima (or just intima) is the innermost layer of an artery or vein. The intima is typically formed by one layer of endothelial cells and is supported by an internal elastic lamina. In the intima the endothelial cells are in direct contact with the blood flow. Adaptive immune responses engaging clonally expanded T cell populations contribute to this inflammatory process, as well as innate immune responses mounted by macrophages and other cells.

Several lines of evidence point to components of the low density lipoprotein (LDL) particles as triggers of vascular inflammation.

The tee a "Low-density lipoprotein" or "LDL" as used herein indicates a type of lipoprotein that transports cholesterol and triglycerides from the liver to peripheral tissues. LDL is one of the five major groups of lipoproteins; these groups include chylomicrons, very low-density lipoprotein (VLDL), intermediate-density lipoprotein (IDL), low-density lipoprotein, and high-density lipoprotein (HDL). Like all lipoproteins, LDL enables fats and cholesterol to move within the water based solution of the blood stream. Typically a native LDL particle contains a single apolipoprotein B (apoB) molecule that circulates the fatty acids, keeping them soluble in the aqueous environment. The apoB on the LDL particle acts as a ligand for LDL receptors in various cells throughout the body. The protein occurs in the plasma in two main isoforms, ApoB48 and ApoB100. The first is synthesized exclusively by the small intestine, the second by the liver. The Apolipoprotein B-100 molecule has 4536 amino acid residues and a MW of about 514 kD. Additionally, LDL has typically a highly-hydrophobic core consisting of a polyunsaturated fatty acid known as linoleate and about 1500 esterified cholesterol molecules. This core is surrounded by a shell of phospholipids and unesterified cholesterol as well as a single copy of the ApoB-100. LDL particles are approximately 22 nm in diameter and have a mass of about 3 million Daltons. Low-density lipoprotein receptors sit on the outer surface of many types of cells, where they pick up low-density lipoproteins circulating in the bloodstream and transport them into the cell. Once inside the cell, the low-density lipoprotein is broken down to release cholesterol. The cholesterol is then used by the cell, stored, or removed from the body. After low-density lipoprotein receptors drop off their cargo, they are recycled back to the cell surface to pick up more low-density lipoproteins. When LDL particles infiltrate the intima, they are prone to undergo oxidative modifications. Such changes likely include enzymatic attacks by myeloperoxidase and lipoxygenases as well as non-enzymatic oxidative reactions. As an initial result of oxidation, double-bonds of fatty acid residues in phospholipids, cholesterol esters and triglycerides are cleaved, generating reactive aldehydes and truncated lipids. Among the latter, modified phospholipids such as lysophosphatidylcholine and oxidized 1-palmitoyl-2-arachidonyl-sn-glycero-3-phosphocholine (ox-PAPC) can activate endothelial cells, macrophages and B1-type B cells to initiate innate immune responses, including adhesion molecule expression, chemokine production, and secretion of natural antibodies. The protein moiety of LDL is also a target of oxidative modifications. They include formation of adducts of malondialdehyde (MDA), 4-hydroxynonenal and other molecular species on lysyl residues of apolipoprotein B-100 (ApoB100). Antibodies are formed to MDA-lysine and other oxidatively generated epitopes of LDL particles (Ketelhuth, D. F., Tonini, G. C., Carvalho, M. D., Ramos, R. F., Boschcov, P., and Gidlund, M. (2008). Autoantibody response to chromatographic fractions from oxidized LDL in unstable angina patients and healthy controls. Scand J Immunol 68, 456-462). Such antibodies circulate in peripheral blood and can also be found in atherosclerotic lesions. In contrast to the natural antibodies to oxidized phospholipids produced by B1 cells, anti-MDA-ApoB100 antibodies are largely IgG molecules (Yla-Herttuala, S., Palinski, W., Butler, S. W., Picard, S., Steinberg, D., and Witztum, J. L. (1994). Rabbit and human atherosclerotic lesions contain IgG that recognizes epitopes of oxidized LDL. Arterioscler Thromb 14, 32-40.). This implies the involvement of T cell help to activate isotype switching in the B cell.

In several embodiments, the method for treating and/or preventing atherosclerosis in an individual herein described comprises inhibiting in the individual a $CD4^+$ T cell response to ApoB100.

The term "T cells" as used herein indicates a group of white blood cells known as lymphocytes, which play a central role in cell-mediated immunity and can be distinguished from other lymphocyte types, such as B cells and natural killer cells by the presence of a special receptor on their cell surface called T cell receptors (TCR). The abbreviation T, in T cell, stands for thymus, since it is the principal organ in the development of the T cell. T cells have been identified both in hypercholesterolemic mice and among clones isolated from human atherosclerotic lesions, the molecular properties of the T cell epitopes are poorly understood due to the biochemical complexity of the LDL particle and the oxidative process. Antibodies are generally produced by plasma cells, which have matured from B lymphocytes in the presence of various cytokines produced by activated CD4+ T lymphocytes and by direct T lymphocyte-B lymphocyte interactions. CD4+ T lymphocytes are activated when they encounter an antigenic peptide with major histocompatibility complex class II antigen-presenting cells, such as B lymphocytes and macrophages. The recognition of major histocompatibility complex class II peptide complexes by T lymphocytes is therefore central to the development of immune responses and antibody production. The major histocompatibility complex class II molecules are highly polymorphic heterodimeric membrane glycoproteins composed of $\alpha$ and $\beta$ chains. The function of major histocompatibility complex class II molecules is to bind short peptides derived mainly from extracellular proteins, in turn forming major histocompatibility complex class II peptide complexes that interact with appropriate T-cell receptors of CD4+ T lymphocytes. At maturity, MHC molecules are anchored in the cell membrane, where they display short polypeptides to T cells, via the T cell receptors (TCRs). All MHC molecules receive polypeptides from inside the cells they are part of and display them on the cell's exterior surface for recognition by T cells.

The term "T cell receptor or TCR" indicates a molecule found on the surface of T lymphocytes (or T cells) that is, in general, responsible for recognizing antigens bound to major histocompatibility complex (MHC) molecules. The TCR is a heterodimer consisting of an alpha and beta chain in 95% of T cells, whereas 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. The variable domain of both the TCR a-chain and β-chain have three hypervariable or complementarity determining regions (CDRs), whereas the variable region of the 13-chain has an additional area of hypervariability (HV4) that does not normally contact antigen and therefore is not considered to be a CDR. CDR3 is the main CDR responsible for recognizing processed antigen, although CDR1 of the alpha chain may also interact with the N-terminal part of the antigenic peptide, and CDR1 of the beta chain interacts with the C-terminal part of the peptide. CDR2 regions interact with the MHC molecule presenting the peptide. The signal from the T cell complex is enhanced by simultaneous binding of the MHC molecules by a specific co-receptor.

The term "$CD4^+$ T cells" as used herein indicates T cells, and in particular helper T cells and regulatory T cells, presenting a co receptor CD4 on their surface. On helper T cells, the CD4 exclusively binds the class II MHC. The co-receptor not only ensures the specificity of the TCR for the correctly-presented antigen but also allows prolonged engagement between the antigen presenting cell and the T cell, thus enhancing the recruitment of essential molecules (e.g. Lck,) inside the cell that are involved in the signaling of that activated T lymphocyte. For example, antigen binding to the T cell receptor (TCR) stimulates the secretion of IL-2 and several other cytokines, and the expression of IL-2 receptors (IL-2R).

In some embodiments, the $CD4^+$ T cell are CD4+T cell presenting a T cell receptor beta variable 31 (TCR TRBV31).

The term "present" as used herein with reference to a compound or functional group indicates attachment performed to maintain the chemical and/or biological reactivity of the compound or functional group as attached. Accordingly, protein presented on a cell is able to perform under the appropriate conditions the one or more chemical and/or biological reactions that chemically and/or biologically characterize the protein.

The term "T cell receptor beta variable 31" or "TRBV31" as used herein indicates T cells carrying the T cell receptor beta variable 31, which is identifiable by a skilled person upon reading of the present disclosure.

The term "T cell receptor beta variable 30" or "TRBV30" as used herein indicates T cells carrying the T cell receptor beta variable 30, which is identifiable by a skilled person upon reading of the present disclosure.

The term "T cell receptor with a DNA sequence highly homologous to that of TRBV31" as used herein denotes T cell receptors the beta domains of which are orthologs of TRBV31, as defined in the TreeFam database (available online). For example, in humans, the ortholog of TRBV31 is TRBV30.

In some embodiments, a compound inhibiting the CD4+T cell response to ApoB100 is used. Such a compound may be a compound identified by its capacity to prevent activation of the hybridoma clone 48-5 upon exposure to apoB100 or a fragment thereof. The hybridoma clone 48-5 has been deposited according to the Budapest Treaty with the DSMZ-Deutsche Sammlung von Mikro-organismen and Zellkulturen GmbH, Inhofftenstrasse 7 B, 38124 Braunschweig, Germany, on Jan. 22, 2009 with the accession number DSM ACC2986.

In some embodiments, inhibiting the CD4+T cell response to ApoB100 is performed by inhibiting the TCR TRBV31.

In some embodiments, inhibiting the CD4+T cell response to ApoB100 is performed by inhibiting a T cell receptor with a DNA sequence highly homologous to that of TRBV31.

In some embodiments, treatment and/or prevention of atherosclerosis and/or a condition associated thereto in an individual, can be performed by administering a therapeutically effective amount of a compound inhibiting the binding of the T cell receptor beta variable 31 (TCR TRBV31) to molecules comprising apolipoprotein B-100 or fragments thereof.

In some embodiments, treatment and/or prevention of atherosclerosis and/or a condition associated thereto in an individual, can be performed by administering a therapeutically effective amount of a compound inhibiting the binding of a T cell receptor with a DNA sequence highly homologous to that of TRBV31 to molecules comprising apolipoprotein B-100 or fragments thereof.

In some embodiments, the binding of the T cell receptor beta variable 31 (TCR TRBV31) to molecules comprising apolipoprotein B-100 or fragments thereof is inhibited.

In some embodiments, the binding of a T cell receptor with a DNA sequence highly homologous to that of TRBV31 to molecules comprising apolipoprotein B-100 or fragments thereof is inhibited.

In some embodiments, inhibition of the CD4+ T cell response to ApoB100 is performed by immunizing the individual against TCR TRBV31 or an immunogenic fragment thereof.

Antigen-specific immunomodulation by vaccination is an attractive approach to prevent or treat chronic inflammatory diseases. By mobilizing protective immune responses in an antigen-specific manner, side effects due to hampered host defense against infections are avoided. Therefore, antigen-specific suppression of pathologic autoimmunity is of interest in chronic inflammatory diseases such as atherosclerosis.

Antigen-specific immunoprotection can be achieved through several different mechanisms, such as production of protective antibodies, deletion or inactivation (anergy) of pathogenic T cell clones, or induction of suppressive cellular immunity mediated by the family of regulatory T cells (Treg).

In some embodiments, immunization can be performed with the TCR TRBV31 protein. In some embodiments, immunization can be performed with a fragment of the TCR TRBV31 and in particular the TRBV31 peptide includes part of the CDR2 variable region of the β chain of the TCR (amino acid residues 45-62, ATGGTLQQLFYSITVGQV—SEQ ID NO: 1) herein also indicated as TRBV31 peptide.

The term "protein" or "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The term "fragment" as used herein indicates a portion of a polypeptide of any length. An antigenic fragment of TCR TVBR31 is accordingly a portion of TCR TVBR31 that presents antigenic properties. Antigenic fragments of TCR TVBR31 herein described also include any peptides however synthesized and possible derivatives thereof.

The term "derivative" as used herein with reference to a first polypeptide (e.g., TCR TVBR31 antigenic fragment), indicates a second polypeptide that is structurally related to the first polypeptide and is derivable from the first polypeptide by a modification that introduces a feature that is not present in the first polypeptide, while retaining functional properties of the first polypeptide. Accordingly, a derivative polypeptide of an antigenic fragment of TCR TVBR31, usually differs from the original polypeptide or portion thereof by modification of the amino acidic sequence that might or might not be associated with an additional function not present in the original polypeptide or portion thereof. A derivative polypeptide of an antigenic fragment of TCR TVBR31 retains however antigenic properties comparable to the ones described in connection with TCR TVBR31 or the antigenic fragment thereof.

In some embodiments, the peptide TCR TRBV31 or a fragment thereof for is described for use as a medicament, and in particular for use in the treatment of atherosclerosis.

In some embodiments, immunization can be performed with antibody reactive to the T cell receptor beta variable 31 (TCR TRBV31) or a fragment thereof.

In some embodiments, antibody reactive to the T cell receptor beta variable 31(TCR TRBV31) or a fragment thereof are described for use as a medicament, and in particular for use in the treatment of atherosclerosis.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an anti-body that specifically binds to and is thereby defined as complementary to a single particular spatial and polar organization of another biomolecule which is termed an "epitope". In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

In some embodiments, proteins (including antibodies), peptides and/or agents for inhibiting T cells response herein described are comprised in a composition together with suitable adjuvant and/or excipients.

The term adjuvant as used herein indicates a pharmacological or immunological agent that modify the effect of other agents (e.g., drugs, vaccines) while having few if any direct effects when given by themselves. They are often included in vaccines to enhance the recipient's immune response to a supplied antigen while keeping the injected foreign material at a minimum. Types of adjuvants include: Immunologic adjuvant that stimulate the immune system and increase the response to a vaccine, without having any specific antigenic effect in itself.

The term excipients as used herein indicates an inactive substance used as a carrier for the active ingredients of a medication. Exemplary excipients can also be used to bulk up formulations that contain very potent active ingredients, to allow for convenient and accurate dosage. In addition to their use in the single-dosage quantity, excipients can be used in the manufacturing process to aid in the handling of the active substance concerned. Depending on the route of administration, and form of medication, different excipients may be used that are identifiable by a skilled person.

In some embodiments, the compositions comprise (immunogenic) peptide fragments of TCR TRBV31 possibly toxins/toxoids: tetanus toxin, diphtheria toxoid, B subunit of cholera toxin, as well as BSA, HAS, rHSA, KLH, ovalbumin.

In some embodiments, the adjuvants and excipients are pharmaceutically acceptable and the resulting composition is a pharmaceutical composition. In some of those embodiments, the pharmaceutical composition is a vaccine.

As disclosed herein, agents for inhibiting the CD4$^+$ T cell response to ApoB100 and/or binding of TCR TRBV31 with ApoB100, in particular the TCR TRBV31, fragments thereof and/or related antibodies, can be provided as a part of systems to treat and/or prevent. The systems can be provided in the form of arrays or kits of parts.

In a kit of parts, the agents and other reagents to perform an assay to detect the inhibiting and/or immunizing can be comprised in the kit independently. The agents can be included in one or more compositions, and each agent can be in a composition together with a suitable vehicle.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of the inhibiting and/or immunizing can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will, usually be included in the kit. The kit can also contain, depending on the particular method used, other packaged reagents and materials (i.e. wash buffers and the like).

In particular, in some embodiments, disclosed are pharmaceutical compositions which contain at least one agent as herein described, in combination with one or more compatible and pharmaceutically acceptable vehicles, and in particular with pharmaceutically acceptable diluents or excipients. In those pharmaceutical compositions the agent can be administered as an active ingredient for treatment or prevention of a condition in an individual.

In some embodiments, use of a hybridoma from mice immunized with oxLDL and carrying human ApoB100 as a transgene (huB100t9) is described to identify suitable agents for inhibition of CD4+ T cell response to ApoB100. In particular, the hybridoma clone 48-5 deposited according to the Budapest Treaty with the DSMZ-Deutsche Sammlung von Mikro-organismen und Zellkulturen GmbH, Inhofftenstrasse 7 B, 38124 Braunschweig, Germany, on Jan. 22, 2009 with the accession number DSM ACC2986 and related uses and systems.

Further details concerning the implementation of the hybridomas, agents, compositions, methods herein described including systems for performance of the methods which can be in the form of kit of parts as well as related compositions including agents and other reagents together with suitable carrier, agent or auxiliary agent of the compositions, and generally manufacturing and packaging of the kit, can be identified by the person skilled in the art upon reading of the present disclosure.

EXAMPLES

The methods and systems herein described are further illustrated in the following examples, which are provided by way of illustration and are not intended to be limiting.

In particular, the following examples illustrate exemplary methods and systems are based on the inhibition of CD4+ T cell response to ApoB100 by immunization performed with a specific peptide from TCR TRBV31. A person skilled in the art will appreciate the applicability of the features described in detail for immunization performed with a different peptide from TCR TRBV31 or for other methods and systems for inhibiting CD4$^+$ T cell response to ApoB100 and in particular CD4$^+$ T cell presenting TCR TRBV31 according to the present disclosure.

In the following examples values are expressed as mean±standard error of the mean (SEM) unless otherwise indicated. Non-parametric Mann-Whitney U test was used for pairwise comparisons. Differences between groups were considered significant with p below 0.05.

Example 1

Of Native Human LDL and ApoB100 by T Cell Hybridomas

For these experiments HuB100tg mice (mice carrying human ApoB100 as a transgene) were used to characterize the T cell response to oxLDL. These mice express human full-length ApoB100 in the liver as well as gut and display a humanized lipoprotein profile.
Immunization For the generation of T cell hybridomas 7-week old male human ApoB100 transgenic mice, huB100tg (C57BL/6,129-Apobtm2sgy, DNX Transgenics, Princeton, USA) were used.

These mice carry the full-length human APOB gene in which codon 2153 has been changed from a leucine to a glutamine to prevent formation of ApoB48, allowing production of ApoB100 only (Boren, J., Lee, I., Zhu, W., Arnold, K., Taylor, S., and Innerarity, T. L. (1998). Identification of the low density lipoprotein receptor-binding site in apolipoprotein B100 and the modulation of its binding activity by the carboxyl terminus in familial defective apo-B100. J Clin Invest 101, 1084-1093; Linton, M. F., Farese, R V., Jr., Chiesa, G., Grass, D. S., Chin, P., Hammer, R E., Hobbs, H. H., and Young, S. G. (1993). Transgenic mice expressing high plasma concentrations of human apolipoprotein B100 and lipoprotein (a). J Clin Invest 92,3029-3037; Yao, Z. M., Blackhart, B. D., Johnson, D. F., Taylor, S. M., Haubold, K. W., and McCarthy, B. J. (1992). Elimination of apolipoprotein B48 formation in rat hepatoma cell lines transfected with mutant human apolipoprotein B cDNA constructs. J Biol Chem 267, 1175-1182.).

The mice were first immunized subcutaneously (s.c.) with 50 μg of copper oxidized human LDL (oxLDL) mixed with complete Freund's adjuvant (CFA) and after 2 weeks the mice were boosted with 50 f. 1 g oxLDL mixed with incomplete Freund's adjuvant (IFA). Oxidized human LDL (oxLDL) was prepared as follows: LDL (d=1.019-1.063 g/mL) was isolated by ultracentrifugation from pooled plasma of healthy donors as described by Havel et al. (Havel, R J., Eder, H. A., and Bragdon, J. H. (1955). The distribution and chemical composition of ultracentrifugally separated lipoproteins in human serum. J Clin Invest 34, 1345-1353). After isolation, LDL was extensively dialyzed against PBS. 1 mM EDTA was added to an aliquot of LDL to be used as unmodified LDL. Highly oxidized LDL was obtained by incubating 1 mL of LDL (1 mg/mL protein content, determined by Bradford, Biorad, USA) in the presence of 20 IJM CUS04 for 18 h, at 37° C.
T Cell Hybridoma Generation After the primary immunization of oxLDL and the booster injection as described above lymph-node (LN) cells were collected and fused with thymoma cells to generate hybridomas as follows:

T cell hybridomas were generated by polyethylene glycol-induced fusion of 5×10$^7$ lymph node cells (LN) with 3×10$^7$ BW5147 thymoma cells as described by Kappler et al. (Kappler, J. W., Skidmore, B., White, J., and Marrack, P. (1981). Antigen-inducible, H-2-restricted, interleukin-2-producing T cell hybridomas. Lack of independent antigen and H-2 recognition. J Exp Med 153, 1198-1214). Briefly, LN cells from the immunized mice were stimulated with 3 μg/ml oxLDL during 3 days before fusion. After fusion, 1×10$^6$ thymocytes were added as feeder cells and the cell suspensions were plated in 96 well plates and incubated at 3rC, 7.5% $CO_2$. Hypoxanthine-aminopterin-thymidine (HAT) was added to the medium after 24 hours of incubation to select successfully fused cells. Among 268 growing hybridoma cultures, 117 were found to express CD3 and CD4. 23 HAT-resistant monoclonal hybridomas were then cloned by limiting dilution and screened for their reactivity against native LDL, copper oxLDL, and purified unmodified ApoB100.
Screening for Positive Clones The 23 HAT-resistant monoclonal hybridomas were assessed for activation by their IL-2 production (antigen binding to the T cell receptor (TCR) stimulates the secretion of IL-2) after exposure to the putative antigen (native LDL, copper oxLDL, and purified unmodified ApoB100) in the presence of syngeneic, irradiated antigen-presenting cells (APC). Such cells take up and process antigens, leading to presentation of antigenic peptides bound to MHC molecules. Syngeneic APC, i.e. APC from mice that carry the same MHC as the T cells are needed in order to prevent activation of T cells recognizing foreign MHC molecules as antigen. T cell reactivity was determined in 96 well plate assays with 1×10$^5$ T hybridoma cells and 4×1 05 irradiated (1.6 Gy) APCs with the different antigens. LDL and oxLDL were prepared as discussed in Example 1. ApoB100 was obtained as previously described by Wessel et al. (Wessel, D., and Flugge, U. I.

(1984) A method for the quantitative recovery of protein in dilute solution in the presence of detergents and lipids Anal Biochem 138, 141-143) with minor modifications. Briefly, to 0.1 ml of LDL (1 mg/mL) 0.4 ml of methanol, 0.1 ml of chloroform, and 0.3 ml of water were added; the suspension was then mixed vigorously and centrifuged at 9000×g for 1 min. The upper phase was removed and 0.3 ml of methanol added to the lower phase and interphase with precipitated protein, which was again vigorously mixed and centrifuged at 9000×g for 2 min to pellet the protein. In order to obtain soluble and highly pure ApoB100, the protein pelleted was resuspended in a minimum volume of 10% SDS (Bio-Rad Laboratories, Hercules, Calif., USA) solution until complete solubilization. These ApoB100 preparations were then subjected to a first filtration using a PD-10 column (GE Healthcare, previously Amersham Biosciences, Uppsala, Sweden) to remove excess of SDS and subsequent purification using size-exclusion column Superdex-200 (0.5 mL/min, in Tris-HCl pH 7.4). The first peak containing ApoB100 was collected and the extra peaks containing contaminant protein from the LDL purification procedure were discarded. ApoB100 preparations showed over 90% purity when evaluated in a second injection to Superdex-200 column (GE Healthcare, Uppsala, Sweden). Finally, protein concentration was determined using Bradford assay (Bio-Rad Laboratories, Hercules, Calif., USA).

APCs were prepared by meshing spleens on nylon filters (1 001-1m) followed by lysis of red blood cells and washing. Concavalin A (ConA) was used as a positive control. Cells were cultured for 24 hours, at 3rC, 7.5% $CO_2$, in Dulbecco's modified Eagle's medium (DMEM) supplemented with 5% fetal calf serum (FCS). Interleukin 2 (IL-2) was measured by ELISA (R&D Systems, Abingdon, United Kingdom) in the supernatant of cultures and used as a read-out for T cell activation. The results can be seen in FIG. 1A wherein $1 \times 10^5$ hybridoma cells of each of the twenty three HAT-resistant monoclonal hybridomas were incubated with $4 \times 10^5$ irradiated APCs together with 40 μg/mL of LDL, oxLDL, or ApoB100. Medium was used as negative control.

Remarkably, from all 23 tested monoclonal T cell hybridomas 11 responded to native human LDL and ApoB100 but none to oxidized LDL.

TCR Genotyping by Polymerase Chain Reaction (PCR)

The eleven clones that could respond to native LDL and ApoB100 were genotyped by PCR. Total RNA was prepared from $1 \times 10^7$ hybridoma cells from each of the 11 hybridoma clones with RNeasy mini kit (Qiagen, Valencia, Calif., USA) and reversely transcribed into cDNA using Superscript II (Invitrogen, Carlsbad, Calif., USA) with random hexanucleotide primers (pdN6) in the presence of RNasin (Life Technologies, Cergy Pontoise, France). The cDNA produced was amplified using appropriate Vα family specific 5' primers (Table 1) together with a constant-region Cα 3' primer, or relevant Vβ family-specific 5' primers (Table 2) together with a constant-region Cβ, 3' primer

TABLE 1

Primers for genotyping of the TRAV

| | α-chain family | Primer sequence | SEQ ID NO |
|---|---|---|---|
| 1 | TRAV01 | 5' TGGATGGTTTGAAGGACAGTG 3' | 2 |
| 2 | TRAV02 | 5' CTGTTTA TCTCTGCTGACCGG 3' | 3 |

TABLE 1-continued

Primers for genotyping of the TRAV

| | α-chain family | Primer sequence | SEQ ID NO |
|---|---|---|---|
| 3 | TRAV03-3 | 5' ACGAAGGACAAGGATTCACTGT 3' | 4 |
| 4 | TRAV04 | 5' CTGGAGGACTCAGGCACTTACT 3' | 5 |
| 5 | TRAV06 | 5' GGTACCCGACTCTTTTCTGGT 3' | 6 |
| 6 | TRAV06D-4 | 5' ACCCTTTCAGAAGATGACTTCC 3' | 7 |
| 7 | TRAV06D-5 | 5' TTT AAAGTCCCAAAGGCCAA 3' | 8 |
| 8 | TRAV06-6 | 5' TCCTGAAAGTCA TTACGGCTG 3' | 9 |
| 9 | TRAV06-7 | 5' AGAGCCTCAAGGGACAAAGAG 3' | 10 |
| 10 | TRAV07-3 | 5' AGACTCCCAGCCCAGTGACT 3' | 11 |
| 11 | TRAV07-5 | 5' ACA TCAGAGAGCCGCAACC 3' | 12 |
| 12 | TRAV080-1 | 5' CCCTGCCCAGCT AA TCTT AA T 3' | 13 |
| 13 | TRAV09-3 | 5' CTGCAGCTGAGATGCAAGTATT 3' | 14 |
| 14 | TRAV090-1 | 5' TCCTATGGTGGATCCATTTACC 3' | 15 |
| 15 | TRAV10 | 5' TGGACAGAAAACAGAGCCAA 3' | 16 |
| 16 | TRAV11 | 5' CAGGCAAAGGTCTTGTGTCC 3' | 17 |
| 17 | TRAV12-1 | 5' ACGCCACTCTCCAT AAGAGCA 3' | 18 |
| 18 | TRAV13-1 | 5' GCTCTTTGCACATTTCCTCC 3' | 19 |
| 19 | TRAV14-1 | 5' TGCAGTTATGAGGACAGCACTT 3' | 20 |
| 20 | TRAV14-3 | 5' CTGCAGTTATGAGAACAGTGCTT 3' | 21 |
| 21 | TRA V15-1/OV6-1 | 5' CCAGACGATTCGGGAAAGTA 3' | 22 |
| 22 | TRAV16 | 5' TTCCATCGGACTCATCATCAC 3' | 23 |
| 23 | TRAV17 | 5' AACCTGAAGAAA TCCCCAGC 3' | 24 |
| 24 | TRAV19 | 5' GGAAGACGGAAGATTCACGTT 3' | 25 |
| 25 | TRAV20 | 5' ACGCTCCT AA TAGACATTCGCT 3' | 26 |
| 26 | TRAV21 | 5' GTTCCTCTTCAGGGTCCAGA 3' | 27 |
| 27 | TRAC | 5' CACCAGCAGGTTCTGGGTTC 3' | 28 |

TABLE 2

Primers for genotyping of the TRBV

| | TCR β-chain family | Primer sequence | SEQ ID NO |
|---|---|---|---|
| 1 | TRBV01 | 5' ACACGGGTCACTGATACGGA 3' | 29 |
| 2 | TRBV02 | 5' ATGGACAA TCAGACTGCCTCA 3' | 30 |
| 3 | TRBV03 | 5' TCACTCTGAAAA TCCAACCCA 3' | 31 |
| 4 | TRBV04 | 5' T AAACGAAACAGTTCCAAGGC 3' | 32 |
| 5 | TRBV05 | 5' ACGGTGCCCAGTCGTTTTA T 3' | 33 |
| 6 | TRBV12-1 | 5' GGATTCCTACCCAGCAGATTC 3' | 34 |

TABLE 2-continued

Primers for genotyping of the TRBV

| | TCR β-chain family | Primer sequence | SEQ ID NO |
|---|---|---|---|
| 7 | TRBV12-2 | 5' AGA T AAAGGAAACCTGCCCAG 3' | 35 |
| 8 | TRBV13-1 | 5' CCAGAACAACGCAAGAAGACT 3' | 36 |
| 9 | TRBV13-2 | 5' GGCT ACCCCCTCTCAGACAT 3' | 37 |
| 10 | TRBV13-3 | 5' TGGCTTCCCTTTCTCAGACA 3' | 38 |
| 11 | TRBV14 | 5' GCGACACAGCCACCT ATCTC 3' | 39 |
| 12 | TRBV15 | 5' CGCAGCAAGTCTCTTATGGAA 3' | 40 |
| 13 | TRBV16 | 5' AT AGATGATTCAGGGA TGCCC 3' | 41 |
| 14 | TRBV17 | 5' TGAGAAGTTCCAA TCCAGTCG 3' | 42 |
| 15 | TRBV19 | 5' GAAGGCT ATGATGCGTCTCG 3' | 43 |
| 16 | TRBV20 | 5' TTCCCATCAGTCATCCCAAC 3' | 44 |
| 17 | TRBV21 | 5' AAAA TGCCCTGCT AAGAAACC 3' | 45 |
| 18 | TRBV23 | 5' CAGCCTGGGAA TCAGAACG 3' | 46 |
| 19 | TRBV24 | 5' GCA TCCTGGAAA TCCTATCCT 3' | 47 |
| 20 | TRBV26 | 5' AGTGTCCTTCAAACTCACCTT 3' | 48 |
| 21 | TRBV29 | 5' AAAGGATACAGGGTCTCACGG 3' | 49 |
| 22 | TRBV30 | 5' GGACAAGTTTCCAA TCAGCCG 3' | 50 |
| 23 | TRBV31 | 5' TTCATCCT AAGCACGGAGAAG 3' | 51 |
| 24 | TRBC1 | 5' TGCAA TCTCTGCTTTTGATGGCTC 3' | 52 |

The nomenclature by the international immunogenetics information system (IMGT) was used for the designation of TCR-V chain usage of T cells. All TCR-V chain sequences were extracted from the IMGT database available online) (Lefranc, M.P., Pommie, C., Ruiz, M., Guidicelli, V., Foulquier, E., Troung, L., Thouvenin-Contet, V., and Lefranc, G. (2003). IMGT unique numbering for immunoglobulin and T cell receptor variable domains and lg superfamily V-like domains. Dev Comp Immunol 27, 55-77). For correspondence between old and new nomenclatures see the IMGT database. The mastermix for PCR reactions contained 10 mM Tris-HCI, 50 mM KCI, 1.5 mM $MgCl_2$, 2 mM dNTP and 0.2 U/ml Taq polymerase (Invitrogen, Carlsbad, Calif., USA). All primers were added to a final concentration of 0.2 µM. The reactions were carried out for 35 cycles using 94 °C. (40 sec) for denaturation, 58 °C. (40 sec) for annealing and 72 °C. (1 min) for polymerization. The PCR products were analyzed on a 1.5% agarose gel and visualized by gel red staining.

Based on TCR genotyping, three different subgroups were identified from the eleven clones that could respond to native LOL and ApoB100, and representative data from each subgroup (15-2, 45-1 and 48-5) are shown together with a non-responding clone 20 (97-3. As can be seen in FIGS. 1B-E there was a clear dose-response for hybridoma clones from each subgroup to the unmodified ApoB100 protein. A characterization of the hybridoma clones with regard to TCR type is given in Table 3 below.

In order to make sure that the responsiveness was not dependent on a humanspecific modification of the protein, LOL and ApoB100 were also isolated from huB100$^{tg}$×Ldlr$^{-/-}$ mice and tested against the hybridomas. These mice produce LDL containing human ApoB100. However, these particles lack posttranslational modifications that occur only in humans and that could hypothetically elicit immune reactions.

In FIGS. 1B-E $1 \times 10^5$ hybridoma cells were incubated with $4 \times 10^5$ irradiated APCs with different concentrations of (□) human ApoB100 purified from human LOL, and (x) transgenic human ApoB100, obtained from huB100$^{tg}$×Ldlr$^{-/-}$ mice. In both experiments, IL-2 secretion was used as readout of activation. From the graph it is seen that this recombinant human ApoB100 was also recognized by the T cell hybridoma subgroups 15-2, 45-1 and 48-5. Therefore, native LDL and human ApoB100 contains the T cell epitope(s) recognized by these T cells.

Example 2

T Cells from Mice Immunized with LDL or oxLDL Recognize Native ApoB100

Having previously established that atherosclerotic lesions contain oligo-clonal T cells and now finding that hybridomas generated from mice immunized with oxLDL can recognize native ApoB100 of LDL, it was questioned whether such autoimmune responses can occur in polyclonal T cell populations. This hypothesis was tested by immunization of huB100$^{tg}$×Ldlr$^{-/-}$ mice with LDL or oxLDL (highly oxidized), followed by an in vitro challenge of spleen cells from these mice with oxLDL or native ApoB100. These mice lack the LDL-receptor that is responsible for eliminating LDL from the circulation. When fed a fatty diet, they develop hypercholesterolemia and atherosclerosis. Immune responses to LDL is increased in this disease condition, making it suitable for analysis of such responses In-Vitro Proliferation Assay Spleen cells from huB100$^{tg}$×Ldlr$^{-/-}$ mice immunized with LDL or oxLDL were isolated and cell suspensions prepared. In 96 well plates, $5 \times 10^5$ spleen cells were incubated in duplicate with different antigens, as described below, in 200 µL of serum-free medium, 1:100 BD ITS+ Premix (BD Biosciences, Franklin Lakes, N.J., USA), 1 mg/mL BSA (Sigma-Aldrich, St. Louis, Mo., USA), 10 mmol/L HEPES (Gibco Invitrogen, Carlsbad, Calif., 25 USA), 1 mmol/L Na pyruvate (Gibco Invitrogen, Carlsbad, Calif., USA), 1 mmol/L nonessential amino acids (Sigma-Aldrich, St. Louis, Mo., USA), and 50 µg/mL gentamycin sulfate (Sigma-Aldrich, St. Louis, Mo., USA) for 72 hours, at 37° C. in a humid 5% $CO_2$ atmosphere. Fifty microliters of $H^3$-Thymidine (Sigma-Aldrich, St. Louis, Mo., USA, 1 µCi in serum-free medium) was added and after 18 h of incubation T cell proliferation was evaluated with a scintillation counter (Wallac, Turku, Finland).

Figure 2:
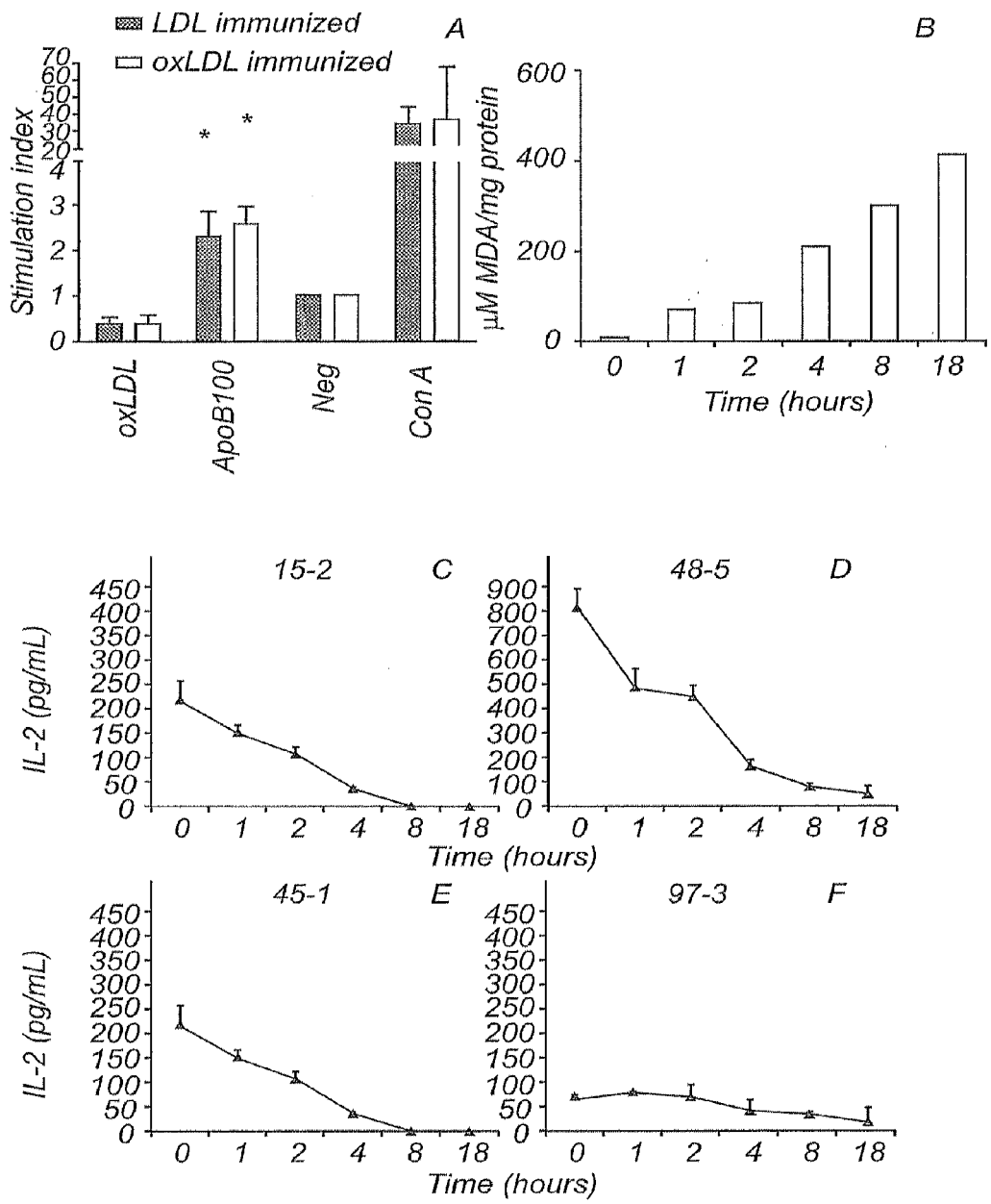
FIGS. 2A-2F show diagrams illustrating results supporting an inverse correlation between oxidation of LDL and T cell activation according to an embodiments herein described.

In FIG. 2(A) $5 \times 10^5$ spleen cells, from huB100×Ldlr$^{-/-}$ mice s.c. immunized with LDL or oxLDL, were challenged in vitro with 20 µ/mL of human oxLDL or native human ApoB100. Values are expressed as mean±SEM of the stimulation index obtained from the H3_Thymidine incorporation. Again, native ApoB100 gave the highest response, whereas oxLDL did not trigger activation (FIG. 2A). Furthermore, this data shows that immunization with either native LDL or oxLDL results in expansion of a T cell population that recognizes native—but not oxidized—epitopes of the LDL particle.

Example 3

Oxidation of LDL Results in Decreased Recognition of the T Cell Epitopes

It was further analyzed the relationship between oxidation and antigenicity of LDL particles by exposing T cell hybridomas to a range of LDL particles that had been oxidized by copper for varying lengths of time, resulting in different degrees of oxidation. Highly oxidized LDL was obtained by incubating 1 mL of LDL (1 mg/mL protein content, determined by Bradford, Biorad, USA) in the presence of 20 ~M CUSO4 for 18 h, at 37° C.; different degrees of oxidation were obtained by incubation of LDL with 20 ~M $CuSO_4$ for 1, 2, 4 or 8 hours. The degree of oxidation was evaluated by TBARS as previously described (Puhl, H., Waeg, G., and Esterbauer, H. (1994). Methods to determine oxidation of low-density lipoproteins. Methods Enzymol 233, 425-441) (FIG. 2B).

Spleen cells from huB100tgxLd/r'-mice immunized with LDL or oxLDL were isolated and cell suspensions prepared as described in Example 2 above. $1.0 \times 10^5$ hybridoma cells from the cell suspensions were incubated for 24 hours with $4 \times 10^5$ irradiated APCs together with 40 ~g/ml of native LDL or oxLDL that had been incubated with 20 ~M $CuSO_4$ for 1, 2, 4, 8 or 18 hours. After 24 hours incubation IL-2 secretion was evaluated in the supernatant of cultured cells (FIG. 2C=15-2 clone; FIG. 2D=48-5 clone; FIG. 2E=45-1 clone; FIG. 2F=97-3 negative control clone).

Surprisingly, there was an inverse relationship between the degree of oxidation and amplitude of activation for all of the T cell hybridomas (FIG. 2C-F). Thus, native LDL gave the highest IL-2 response, whereas heavily oxidized LDL (i.e. LDL that had been oxidized for 18 hours) did not trigger any activation at all. Effects of oxLDL on cell viability after incubations was tested and showed no significant difference between groups (data not shown). These data suggest that the T cell response to epitopes in LDL is gradually diminished upon oxidation.

Example 4

T Cell Responses to Native LDL and ApoB100 Depend on Specific MHC Class II Molecules Since purified ApoB100 was able to induce activation of the CD4+ T cell hybridomas obtained from the immunized mice, it was hypothesized that the epitopes would be peptides presented by the MHC class II complex; in the case of the present mice, the I-$A^b$ haplotype. For evaluation of MHC class II restriction, $1 \times 10^5$ hybridoma cells were incubated with $4 \times 10^5$ irradiated APCs, taken from mice that are either syngeneic donors (C57BL6; I-$A^b$) i.e. I-$A^b$ haplotypes, or from mice of a different genotype (BALB/c; I-$A^d$), 5 i.e. I-$A^d$ haplotypes, together with different concentrations of human ApoB100. In parallel, hybridoma cells were challenged with ApoB100 in the presence of irradiated APCs of the I-$A^b$ haplotype, together with anti-MHC class II blocking antibody. After 24 hours incubation IL-2 secretion was evaluated in the supernatant of cultured cells. A=15-2 clone; B=48-5 clone; C=45-1 clone; D=97-3 negative control clone.

Figure 3:
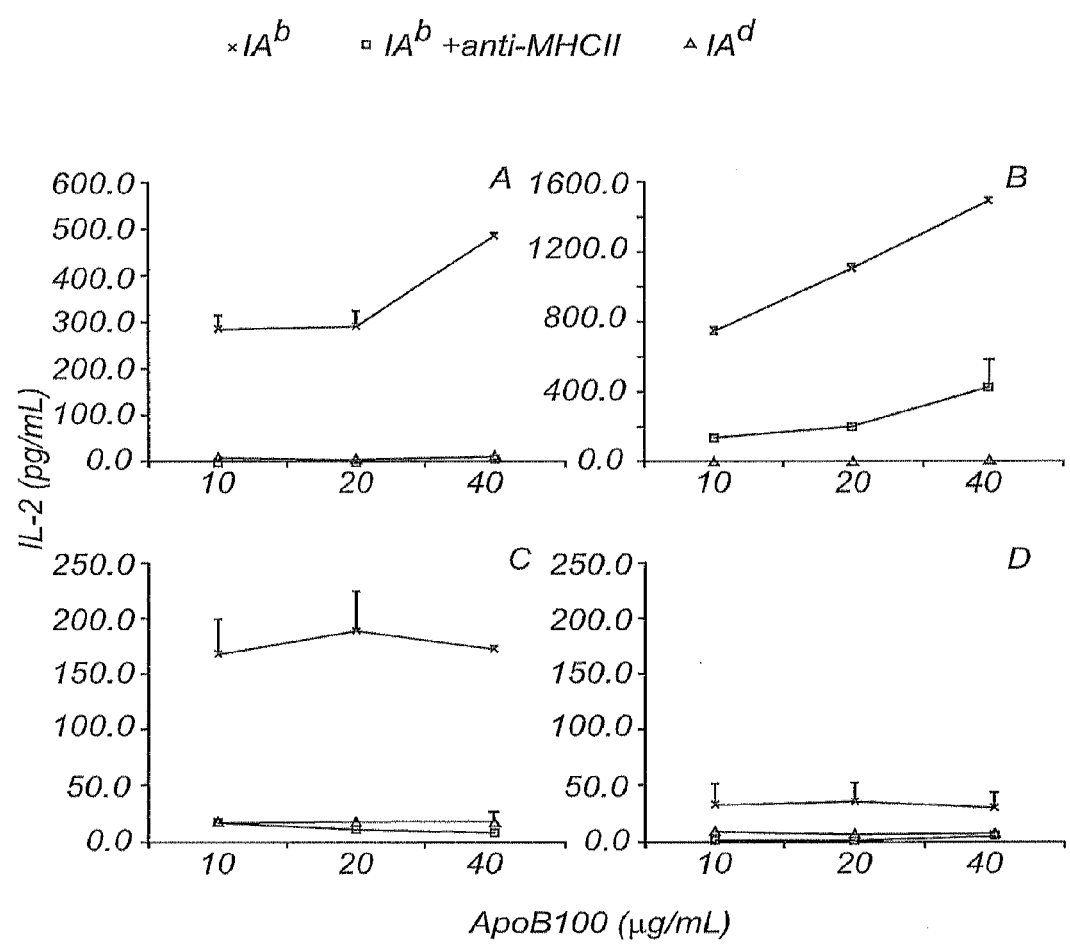
FIGS. 3A-3D show diagrams illustrating results supporting that in an embodiment herein described hybridoma responses are I-$A^b$ restricted.

It can be seen in FIG. 3 that when a blocking antibody against mouse I-$A^b$ was added, there was a clear suppression of T cell activation for all clones. Mismatched I-$A^d$ expressing APCs from BALB/c mice could not present ApoB100 to antigen-specific T cell hybridomas. Therefore, recognition of ApoB100 protein by antigen specific T cells requires that antigenic protein components are presented by syngeneic MHC class II molecules.

Figure 4:
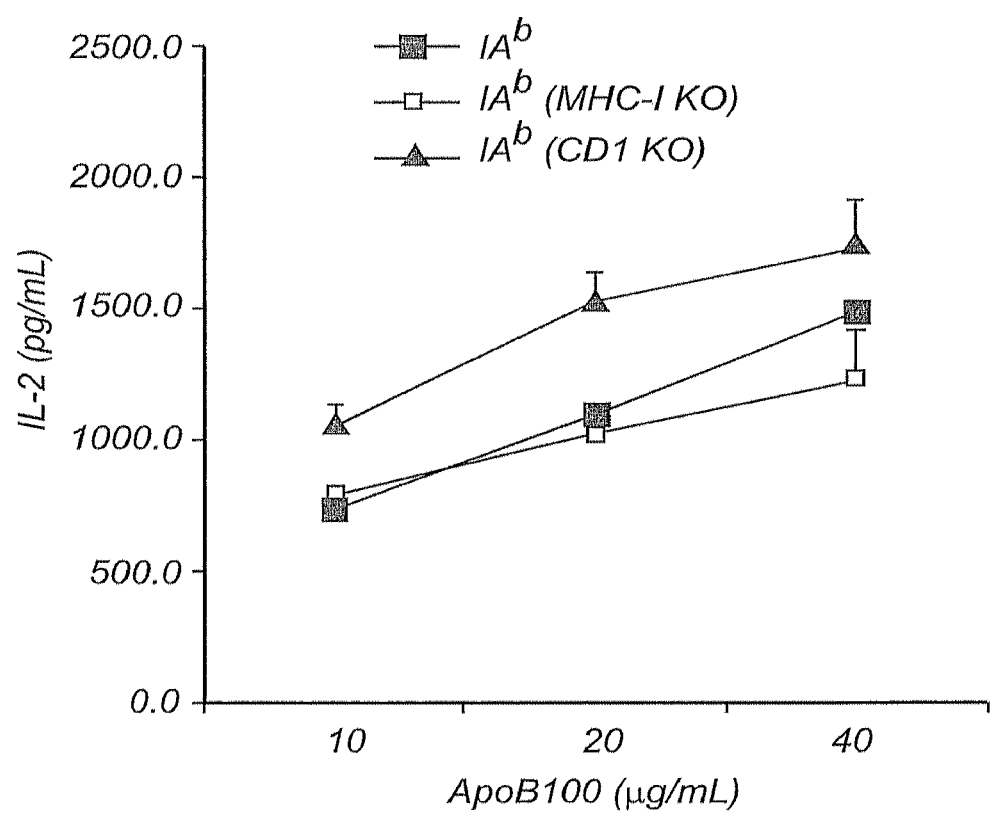
FIG. 4 shows a diagram illustrating results supporting that in an embodiment herein described hybridoma response is not dependent of CD1 and MHC-I presentation.

To test if lipid antigens bound to or possibly co-purified with ApoB100 were involved, T cell responses to ApoB100 presented by APCs carrying I-$A^b$ but lacking CD1d, an MHC-like molecule that presents lipid antigens to T cells, were assessed. However, lack of CD1d on APCs did not impair the T cell response (FIG. 4). Similarly, APCs from I-$A^b$ mice lacking MHC class I molecules were able to present ApoB100 antigens to T cell hybridomas (FIG. 4). These results show that ApoB100 antigen is recognized by MHC class II restricted CD4+ T cells. Together, the experiments described in this example indicate that cellular immune responses to apoB100 are mounted by T cells of the CD4+ type and require antigen presentation involving MHC class II molecules on APC carrying the same MHC type as the responding T cells. Such a scenario is characteristic of classical presentation to T cells of peptide antigens taken up from the extracellular space.

Example 5

T Cells Reactive to Native LDL and ApoB100 Express TRBV31

The TCR of T cell hybridomas were characterized on the mRNA level using RT-PCR amplification of rearranged variable domains. RNA isolation and cDNA synthesis was performed as mentioned in Example 1.

The cDNA produced was amplified using appropriate Vβ family-specific 5' primers (Table 2) together with a constant-region Cβ 3' primer, or relevant Vα family-specific 5' primers (Table 1) together with a constant-region Cα 3' primer. The design of all primers was based on previously published sequences (Lefranc, M. P., Pommie, C., Ruiz, M., Giudicelli, V., Foulquier, E., Truong, L., Thouvenin-Contet, V., and Lefranc, G. (2003). IMGT unique numbering for immunoglobulin and T cell receptor variable domains and Ig superfamily V-like domains. Dev Comp Immunol 27, 55-77). The mastermix for PCR reactions contained 10 mM Tris-HCl, 50 mM KCl, 1.5 mM $MgCl_2$, 1 mM dNTP and 0.2 U/ml Taq polymerase (Invitrogen). All primers were added to a final concentration of 0.2 μM. The reactions were carried out for 35 cycles using 94° C. (40 seconds) for denaturation, 56° C. (40 seconds) for annealing and 72° C. (1 minute) for polymerization. The PCR products were analyzed on a 1.5% agarose gel and visualized by ethidium bromide staining.

Real time-PCR was carried out using assay-on-demand primers and probes for CD3 and hypoxanthine guanidine ribonucleosyl transferase (HPRT) (Applied Biosystems, Foster City, Calif., USA) in an ABI 7700 Sequence Detector (Applied Biosystems, Foster City, Calif., USA).

For quantitative TRBV31 expression analysis, genotyping primers were used in combination with a probe that was designed based on the nucleotide sequences of the constant region of TCR β chain (5'-TCCACCCAAGGTCT-3'-SEQ ID NO:53). The probe was designed using ABI Primer Express software (Applied Biosystems, Foster City, Calif., USA) and it was synthesized with a 6-carboxy-fluorescein (FAM) reporter molecule attached at the 5' end (Applied Biosystems, Foster City, Calif., USA). Data was analyzed on the basis of the relative expression method with the formula 2-ΔΔCT, where ΔΔCT=ΔCT (sample)−ΔCT (calibrator=average CT values of all samples within each group), and ΔCT is the CT of the housekeeping gene (HPRT) subtracted from the CT of the target gene (Giulietti, A, Overbergh, L., Valckx, D., Decallonne, B., Bouillon, R., and Mathieu, C. (2001). An overview of real-time quantitative PCR: applications to quantify cytokine gene expression. Methods (San Diego, Calif. 25, 386-401). The results are summarized in Table 3.

TABLE 3

| | PCR | | Flow cytometry | | | Resulting |
|---|---|---|---|---|---|---|
| | Vα gene | Vβ gene | Anti-TRAV14 | Anti-TRAV12 | Anti-TRAV31 | phenotype |
| 15-2 | TRAV14, 3 and 20 | TRBV31 and 12.1 | negative | — | Positive | TRAV3/TRBV31 |
| 45-1 | TRAV4 and 20 | TRBV31 and 12.1 | — | — | Positive | TRAV4/TRBV31 |
| 48-5 | TRAV12, 13 and 20 | TRBV31 and 12.1 | — | Negative | Positive | TRAV13/TRBV31 |

Figure 5:
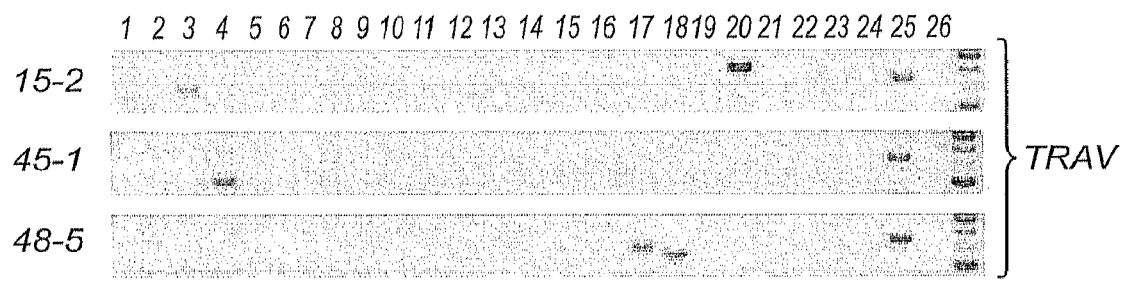
FIG. 5 shows results of experiments supporting genotyping of the T Cell Receptor (TCR) in an embodiment herein described.
Figure 5:
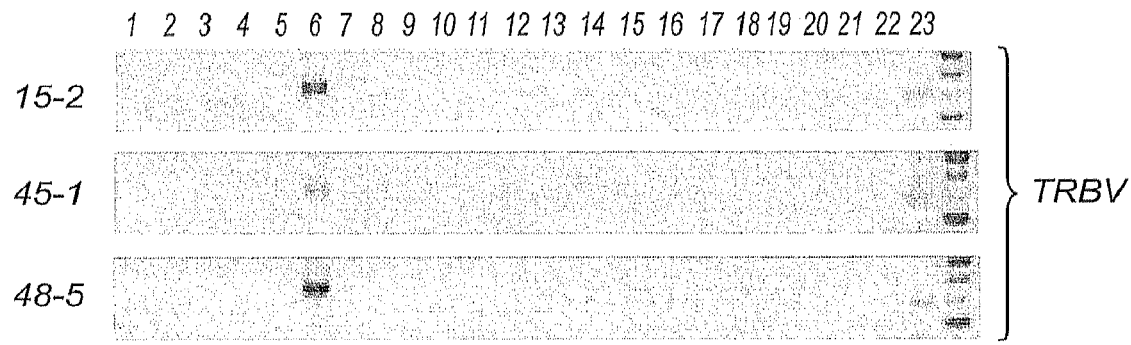
Figure 6:
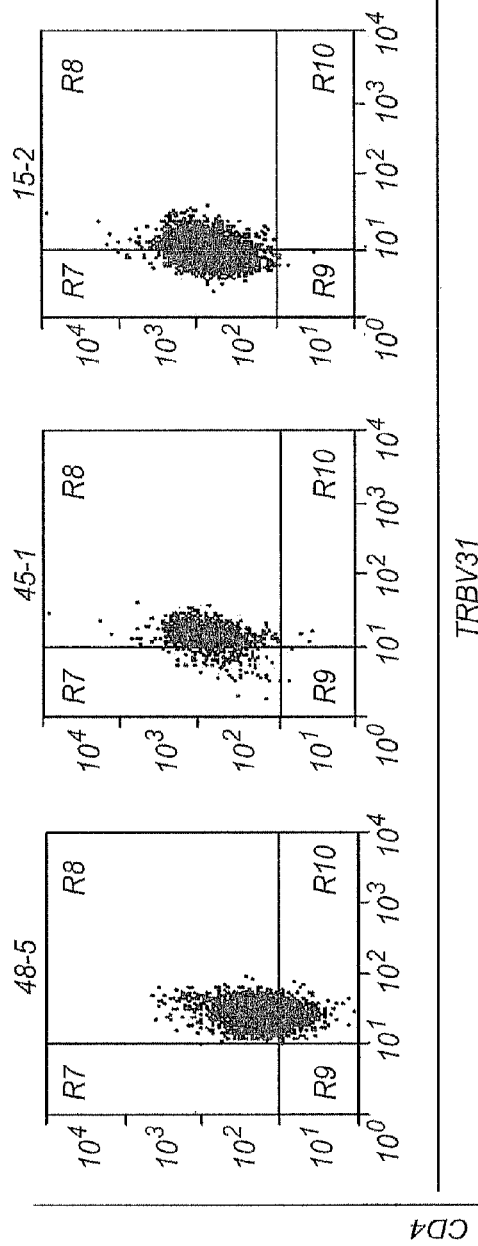
FIG. 6 shows diagrams illustrating results related to TCR expression evaluated by FACS in an embodiment herein described.
Figure 6:
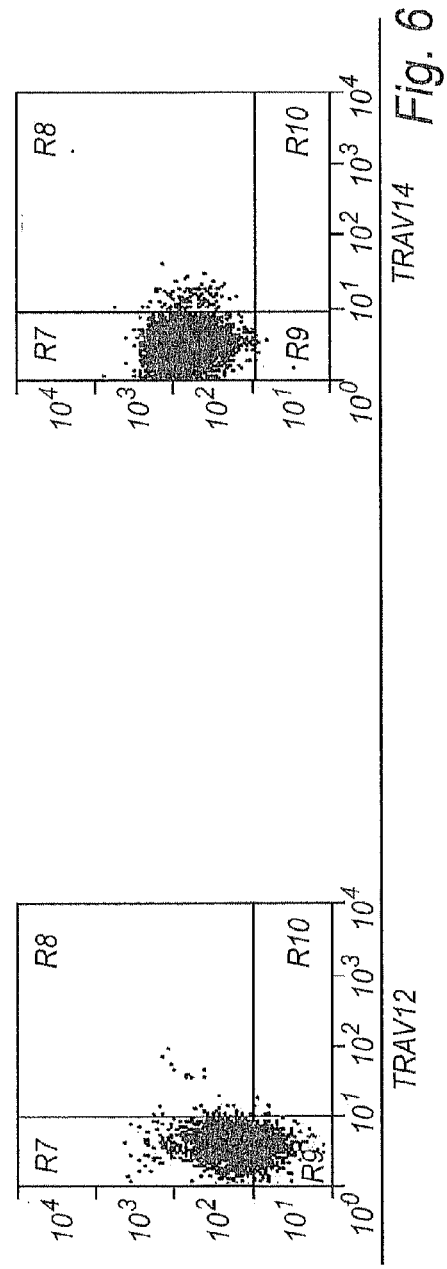

The fusion-partner thymoma BW5147 used to generate the hybridoma cells (see Example 1) expressed the rearranged TRAV20 and TRBV12.1 variable chains and all hybridomas were also expressing these chains at the mRNA level (Tables 1, 2 and 3 and FIG. 5). All T cell hybridomas specific for native human LDL and ApoB 100 uniformly expressed the TCR TRBV31 (T cells carrying the T cell receptor beta variable 31) and no other Vβ family was identified among them. In contrast, the usage of Vα chains among the reactive hybridomas included different families; TRAV3, 4 and 13 for 15-2, 45-1 and 48-5 respectively (Table 3). For the non-reactive hybridomas, Vβ as well as Vα TCR variable chains were expressed in a non-restricted fashion, and did not include TRBV31 (data not shown). In each one of the LDL-responsive hybridomas, surface expression of the TRBV31 T cell receptor chain was confirmed by flow cytometry analysis (Table 3 and FIG. 6). All commercially available anti-mouse TCR-Vα and TCR-Vβ monoclonal antibodies (mAb, BD PharMingen, San Diego, Calif., USA) were used to stain the TCR-Vα and TCR-Vβ on the selected T cell hybridomas. The TCR-V mAbs were conjugated to PE, FITC or biotin/streptavidin-Cy5. In combination with these antibodies, anti-CD3-Pacific Blue and anti-CD4-APC were used. Spleen cells from non-immunized mice were used as positive controls for all antibodies. The cells were analyzed on a CyAn™ ADP flow cytometer (Dako, Glostrup, Denmark).

Example 6

Depletion of TRBV31⁺ T Cells Reduces the Proliferative Response to ApoB100

To directly test the overall importance of the TRBV31 variable chain for the recognition of ApoB100, mice were immunized and boosted with ApoB100 followed by in vitro depletion of TRBV31+T cells from spleen. HuB100$^{tg}$× Ldlr$^{-/-}$ mice were immunized and boosted s.c. with ApoB100. Spleen cells were harvested and followed by in vitro depletion of TRBV31+ or TRBV19+ T cells from spleen by Fluorescence-Activated Cell Sorting (FACS). 60×10⁶ spleen cells were split in 2 and stained separately with anti-TRBV31 and anti-TRBV19 (PharMingen, San Diego, Calif., USA) respectively. TRBV19 was used as a control for the sorting procedure since none of the hybridomas recognizing ApoB100 presented TRBV19 usage. Of note, the clones 96.7 and 97.3, expressing the TRBV191TRAV13.2 chains with no recognition of LDL or ApoB100, did show reactivity to HDL (data not shown). After staining the cells they were sorted in a MoFlo Cytomation cell sorter (Cytomation Bioinstruments, Freiburg, Germany) for the depletion of positive events. Negative cells were then collected and used in the proliferation assay against ApoB100.

Figure 7:
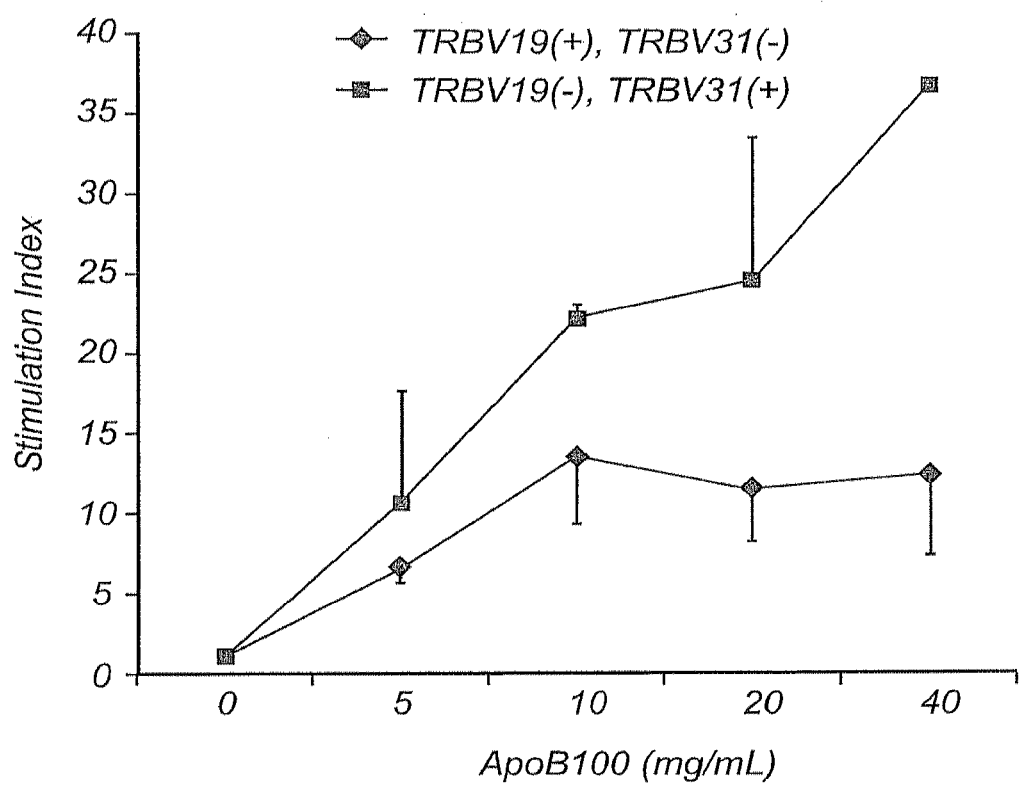
FIG. 7 shows a diagram illustrating results indicating plasma levels of cholesterol and triglycerides according to an embodiment herein described.

Thereafter 5×10⁵ TRBV31+/TRBV19− or TRBV19+/TRBV31− spleen cells were challenged in vitro with different concentrations of human ApoB100. Stimulation index was obtained by H3-thymidine incorporation as described in Example 2. The depletion of TRBV31+ T cells from spleen led to a significant reduction in the response to the ApoB100 antigen upon in vitro challenge, which was not observed when T cells expressing the variable chain, TRBV19, were depleted from the spleenocyte population (FIG. 7). Therefore, a significant proportion of the cellular immune response to ApoB100 in this model is carried out by TRBV31+ T cells.

Example 7

Immunization Against TRBV31+TCR Protects Against Atherosclerosis

To determine the impact on atherosclerosis of the ApoB100-reactive TRBV31+ T cell population, huB100$^{tg}$× Ldlr$^{-/-}$ mice were immunized with a peptide derived from TCR TRBV31. In these experiments, eleven week-old male huB100$^{tg}$×Ldlr$^{-/-}$ mice (C57BL/6, 129-Apob$^{tm2Sgy}$Ldlr$^{tm1Her}$ (Skalen, K., Gustafsson, M., Rydberg, E. K., Hulten, L. M., Wiklund, O., Innerarity, T. L., and Boren, J. (2002). Subendothelial retention of atherogenic lipoproteins in early atherosclerosis. Nature 417, 750-754) kindly provided by Jan Boren, Göteborg University) were used. These mice have an elevated serum 30 cholesterol level of 200-400 mg/dl and they have very high levels (>2,000 mg/dl) when fed a high fat diet. The mice were immunized s.c. with 100 µg of TRBV31 peptide This TRBV31 peptide includes part of the CDR2 variable region of the β chain of the TCR (amino acid residues 45-62, "ATGGTLQQL-FYSITVGQV"—SEQ ID NO:1). The peptide is synthesized and conjugated to keyhole limpet hemocyanin (KLH) by Anaspec, San Jose, Calif., USA).

KLH is a natural protein isolated from the marine mollusk keyhole limpet and is an immunogenic carrier protein that, in vivo, increases antigenic immune responses to haptens and other weak antigens such as idiotype proteins. The TRBV31 peptide-KLH conjugate was emulsified with complete Freund's adjuvant, and the mice were boosted 4 weeks later with the same antigen emulsified with IFA. A control group of mice was immunized s.c. with 100 µg of KLH using the same protocol as for the peptide. The mice were kept on high fat diet (0.15% cholesterol) starting 5 days after the immunization until sacrifice 10 weeks later with CO₂. In addition, irradiated spleen cells from mice on C57BL16 background were used as antigen presenting cell (APC) in the hybridoma experiments. All experiments were approved by the local ethics committee.

Figure 8:
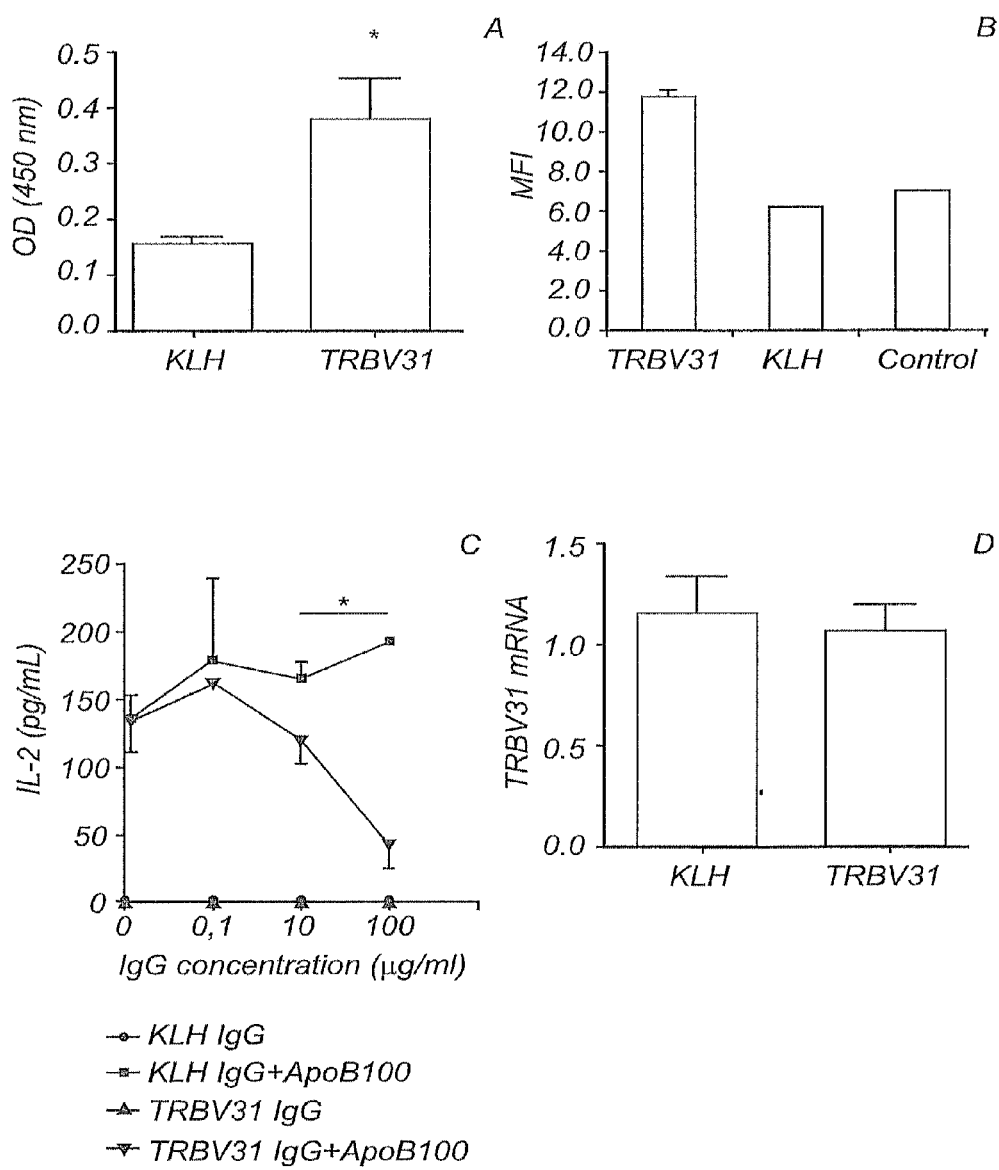
FIGS. 8A-8D show diagrams illustrating results indicating antibody titers to oxLDL and LDL in an embodiment herein described.

Subcutaneous immunization with this TRBV31 peptide, representing part of the CDR2 domain and fused to a carrier protein, in Freund's adjuvant induced the production of antibodies to TCR TRBV31 (FIGS. 8A-D). The titers of specific antibodies to TRBV31 were measured by ELISA. Briefly, 50 µL of the TRBV31 peptide (5 µg/mL in PBS pH 7.4) were added to 96 well ELISA plates and incubated overnight at 4° C. Coated plates were washed with PBS and thereafter blocked with 1% Gelatin (Gibco Invitrogen, Carlsbad, Calif., USA) in PBS for 1 hour, at room temperature. Next, plates were washed and followed by 2 more hours of incubation with mouse plasma diluted in Tris buffered saline (TBS)/gelatine 0.1%. After washing, total IgG, and igG isotypes were detected using enzyme-conjugated anti-mouse antibodies (BD Biosciences, Franklin Lakes, N.J., USA). The plates were washed and the color reaction developed using TMB substrate reagent (BD Biosciences, Franklin Lakes, N.J., USA). The absorbance was measured using a microplate reader (VersaMax, Molecular Devices, Sunnyvale, Calif., USA). FIG. 8A shows IgG antibody titers to TRBV31 peptide measured by ELISA. This data demonstrates that immunization induced high-titer antibodies to the peptide dervived from TRBV31.

Affinity purified circulating IgG antibodies from immunized mice stained LDL-reactive TRBV31+hybridomas (48-5 clone) (FIG. 8B), indicating that these IgG antibodies bound to TCR of such cells. Total IgG plasma antibodies from KLH or TRBV31 immunized mice were affinity purified using a protein-G column (GE healthcare, Uppsala, Sweden). $1 \times 10^4$ hybridoma cells (clone 48-5) were cultured with 40 μ/mL of ApoB100 in the presence of $4 \times 10^4$ irradiated APCs. For the blocking of hybridoma activation, the different antibodies (KLH IgG or TRBV31 IgG) were added at the beginning of culture, at the concentrations 0.1, 1, 10 and 100 μg/ml, as indicated in FIG. 8C and were present throughout. After 24 h of incubation, IL-2 was measured in the supernatant. In FIG. 8C it can be seen that IgG from TRBV31-peptide immunized mice inhibited activation of T cell hybridoma (clone 48-5) in response to ApoB100. Thus, immunization led to production of antibodies that prevented TCR TRBV31 recognition of antigen. The Hybridoma clone 48-5 has been deposited according to the Budapest Treaty with the DSMZ-Deutsche Sammlung von Mikro-organismen und zellkulturen GmbH, Inhoffenstraβe 7 B, 38124 Braunschweig, Germany, on Jan. 22, 2009 with the accession number DSM ACC2986.

Finally, the role of TRBV31$^+$ T cells in atherosclerosis was tested in experiments with HuB100$^{tg}$×Ldlr$^{-/-}$ mice. These animals were immunized with the TRBV31-peptide conjugated to KLH carrier protein, followed by a single booster injection; atherosclerotic lesions were analyzed 10 weeks after immunization. Mice that were immunized with KLH only were used as control.

Figure 9:
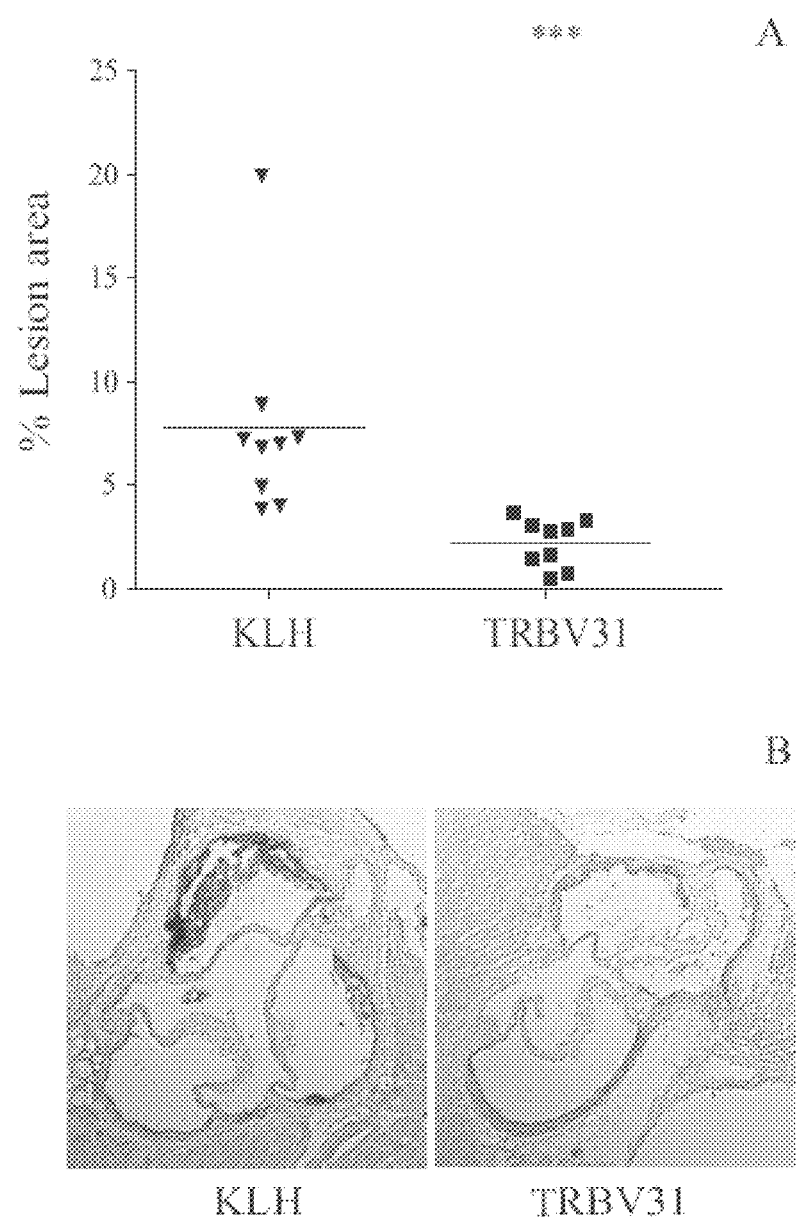
FIGS. 9A-9B show a diagram and a photographic representation indicating that, in an embodiment herein described, TRBV31 + cell-depletion reduces the T cell response to ApoB100.

After sacrifice, blood from mice was collected through cardiac puncture. This was followed by vascular perfusion with sterile RNase-free PBS. Thoracic aorta and heart were dissected and saved for lesion analysis. Two thirds of the spleen was saved for cell experiments and one third snap-frozen for later RNA isolation. Draining lymph nodes from the inguinal region and also the abdominal aorta were snap-frozen and saved for RNA isolation. Lesion analysis was performed as described previously (Nicoletti, A., Kaveri, S., Caligiuri, G., Bariety, J., and Hansson, G. K. (1998). Immunoglobulin treatment reduces atherosclerosis in apo E knockout mice. J Clin Invest 102, 910-918). Briefly, hearts were subjected to serial cryostat sections from the proximal 1 mm of the aortic root. Hematoxylin/oil red O-stained sections were used for lesion size evaluation using Image J software (NIH, Bethesda, Md., USA). In FIG. 9A the mean lesion size was determined after measuring 8 sections collected at every 100 I-lm over a 1-mm segment of the aortic root. FIG. 9B shows images captured for each section and the surface areas of the lesion(s) and of the entire vessel were measured. The fraction area lesion (%) is the ratio between the cross-section area occupied by lesion and the total vessel cross-section area.

It can be seen that immunization with the TRBV31-peptide led to a dramatic and highly significant 70% reduction of lesion size in the aortic root as compared to control mice immunized with KLH carrier protein alone (P<0.01).

Figure 10:
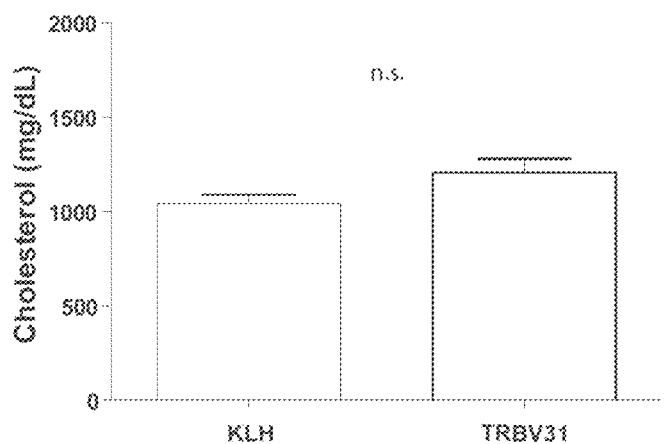
FIGS. 10A-10B show diagrams illustrating results indicating that, in an embodiment herein described immunization against TRBV31 induces blocking antibodies.
Figure 10:
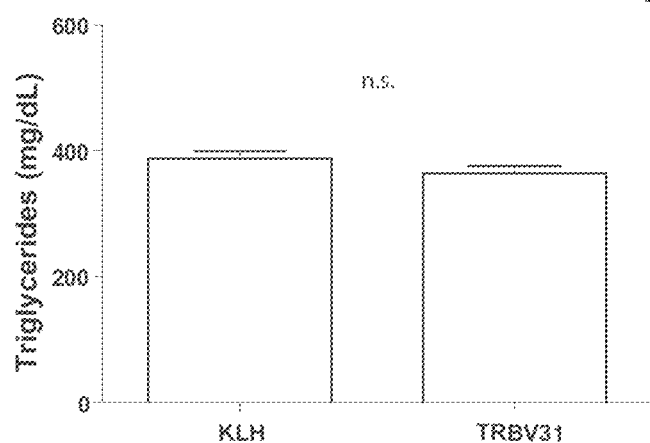
Figure 11:
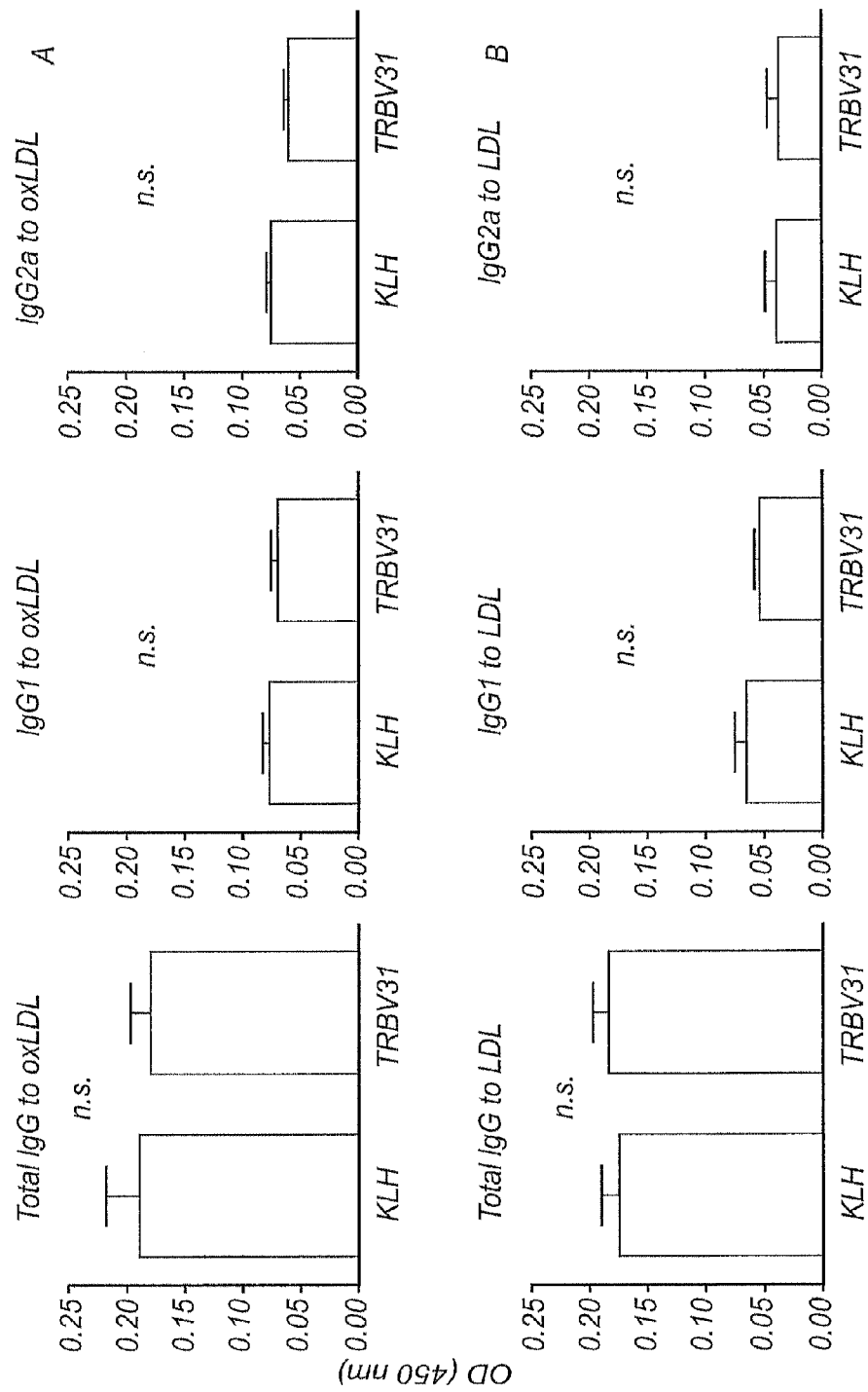
FIGS. 11A-11B show diagrams illustrating results indicating that, in an embodiment herein described, immunization against TRBV31 reduces atherosclerosis.

This effect was paralleled by induction of anti-TRBV31 antibodies but did not affect antibody titers to oxLDL, plasma cholesterol or triglyceride levels (FIGS. 10 and 11).

Plasma cholesterol and triglycerides were evaluated by enzymatic colorimetric specific kits (Randox Lab. Ltd. Crumin, UK) according to the manufacturer's protocol.

TCR TRBV31 mRNA was quantified by real time-PCR in aorta of both immunized groups as follows: RNA isolation and cDNA synthesis was performed as previously mentioned (see above). Real time-PCR was carried out using assay-on-demand primers and probes for CD3 and hypoxanthine guanidine ribonucleosyl transferase (HPRT) (Applied Biosystems, Foster City, Calif., USA) in an ABI 7700 Sequence Detector (Applied Biosystems, Foster City, Calif., USA). For TRBV31 expression analysis, the genotyping primers were used in combination with a probe that was designed based on the nucleotide sequences of the constant region of TCR 13 chain (5'-TCCACCCAAGGTCT-3—SEQ ID NO:54). The probe was designed using ABI Primer Express software (Applied Biosystems, Foster City, Calif., USA) and it was synthesized with a 6-carboxy-fluorescein (FAM) reporter molecule attached at the 5' end (Applied Biosystems, Foster City, Calif., USA). Data was analyzed on the basis of the relative expression method with the formula 2ΔΔCT, where ΔΔCT=ΔCT (sample)−ΔCT (calibrator=average CT values of all samples within each group), and ΔCT is the CT of the housekeeping gene (HPRT) subtracted from the CT of the target gene (Giulietti et al., 2001).

TCR TRBV31 in RNA was present in the aorta of immunized as well as control mice (FIG. 10D), confirming that this population of T cells was not eliminated but prevented from recognizing their cognate antigen. In conclusion, abrogation of TCR TRBV31 recognition of native ApoB100 protein inhibits atherosclerosis.

It is evident that oxLDL particles trigger a strong immune response (for example, see Palinski, W., Yla-Herttuala, S., Rosenfeld, M. E., Butler, S. W., Socher, S. A., Parthasarathy, S., Curtiss, L. K., and Witztum, J. L. (1990). Antisera and monoclonal antibodies specific for epitopes generated during oxidative modification of low density lipoprotein. Arteriosclerosis 10, 325-335 and Zhou X et al, Arterioscler Thromb Vasc Biol 21: 108-114, 2001). Since T-cell dependent antibodies are formed to aldehyde adducts on ApoB100 and exposure of APC-T cell cultures to oxLDL can elicit CD4+ T cell activation, it has been assumed that T cells recognize epitopes on ApoB100 induced by oxidation of the native apolipoprotein. Instead, the present invention shows that T cells from oxLDL immunized mice preferentially recognize motifs on native LDL. These epitopes are components of the native ApoB100 protein and their immunoreactivity is extinguished rather than increased by oxidative modification of the LDL particle.

The cellular immune response to LDL identified in the present study was mounted by CD4+ T cells and exhibited MHC class II restriction. This and the fact that purified ApoB100 protein elicited an identical response as the intact LDL particle strongly suggest that intracellular processing of ApoB100 in the antigen-presenting cell generated oligopeptide epitopes that were recognized by the T cells as peptide-MHC complexes. The fact that I-Ab was required for the T cell response and could not be substituted by another MHC class II molecule, I-Ad, further supports the notion that specific oligopeptides bound to MHC constitute the ligand with which clonotypic TCR could interact.

Since APC have such a high capacity to present ApoB100 epitopes, there is a significant risk for autoimmune reactions to LDL. Systemic reactions of this kind could obviously be detrimental since LDL is present throughout the circulatory system and in all organs. It was previously assumed that all ApoB100 reactive T cell clones were deleted in the thymus during early life, i.e. autoimmunity is avoided by central tolerance. The current data rule out this possibility. It was clearly demonstrated that LDL reactive T cells were present in huApoB100$^{tg}$×Ldlr$^{-/-}$ mice. In line with these findings, it has been suggested that the immune system may not be tolerized at all toward many peripheral antigens, and that the existence of autoreactive T cells per se may not pose an autoimmune danger in the healthy individual. Consequently, ApoB1OO-reactive T lymphocytes are most likely part of the peripheral cell repertoire.

If autoreactivity is not completely eliminated by central tolerance in early life, autoimmune reactions must be avoided by peripheral tolerance mechanisms. They depend on active inhibition of autoreactivity, e.g. by cells secreting immunoregulatory cytokines such as M2 macrophages and regulatory T cells. Furthermore, proteins synthesized in the liver have been reported to preferentially induce tolerogenic immunity. Since ApoB100 is produced in the liver, it may escape autoimmune attack under normal circumstances. However, accumulation in the artery wall under conditions that favor activation of Th1 effector cells may lead to break of tolerance and induction of immune reactions to ApoB100 components.

The present data pinpoint CD4+ T cells carrying TCR TRBV31 and recognizing native ApoB100 protein of LDL as proatherogenic contributors to the disease process. However, they do not rule out the involvement of other antigens and immune cells. Thus, it cannot be ruled out that certain types of LDL modifications induce autoimmune reactions towards the particle. The oxidative changes induced in the particle in vivo may differ from those induced by metal ions such as copper. Furthermore, the hybridoma strategy provides detailed information on a small subset of cells and certain reactivities may not have been represented in the hybridoma repertoire analyzed. Finally, the present strategy focused on antigens presented by professional APC through the endocytic, MHC class II restricted pathway to CD4+ T cells. Additional important contributions to LDL immunoreactivity may arise from NKT cells recognizing lipid antigens presented via CD1, CD8+ T cells recognizing MHC class I restricted antigens and B cells.

Immunization of atherosclerosis-prone huApoB100× Ldlr$^{-/-}$ mice against TCR TRBV31 provided important insights into the immunopathology of atherosclerosis. Antibodies isolated from hyperimmune sera blocked activation of T cells in response to ApoB100, and elimination of TCR TRBV31+ cells by flow cytometry blunted T cell responses to ApoB100 in spleen cell cultures. However, antibodies induced by the present immunization strategy blocked antigen recognition by TCR TRBV31+cells but did not eliminate them from aorta.

The induction of blocking anti-TRBV31 antibodies was associated with a 70% reduction of atherosclerosis in huApoB100$^{tg}$×Ldlr$^{-/-}$ mice. The magnitude of reduction is even better than that achieved by immunization with LDL preparations in similar models Urban, R. G., Chicz, R. M., and Strominger, J. L. (1994). Selective release of some invariant chain-derived peptides from HLA-DR 1 molecules at endosomal pH. J Exp Med 180, 751-755; Freigang, S., Horkko, S., Miller, E., Witztum, J. L., and Palinski, W. (1998). Immunization of LDL receptor-deficient mice with homologous malondialdehyde-modified and native LDL reduces progression of atherosclerosis by mechanisms other than induction of high titers of antibodies to oxidative neoepitopes. Arterioscler Thromb Vasc Biol 18, 1972-1982) and therefore strongly suggests that a subset of T cells recognizing ApoB100 epitopes play a major role in the development of atherosclerosis. Since TCR TRBV31 did not disappear from the aorta after immunization, blocking their recognition of MHC-antigen complexes may suffice to inhibit the disease process.

The use of the huApoB100$^{tg}$×Ldlr$^{-/-}$ model permitted the use of well defined human LDL preparations for dissecting the cellular autoimmune response in atherosclerosis.

According to the above examples T cell recognition of oxLDL, T cell hybridomas from mice immunized with oxLDL were created, which mice were carrying human ApoB100 as a transgene (huB100$^{tg}$). These mice produce high levels of ApoB100 and are also expected to be tolerant to native human LDL.

Hence the experiments exemplified in the above examples show that to great surprise, T cell responses against native LDL and purified ApoB100 in such mice carrying T cell hybridomas from mice immunized with oxLDL and carrying human ApoB100 as a transgene (huB100t9) were registered, whereas oxidation of LDL blunted these responses. The responding T cells were MHC class II restricted CD4+ cells and expressed a T cell receptor (TCR) containing a variable 13 domain of the TRBV31 type. Elimination of TRBV31+ T cells attenuated the cellular immune response to ApoB100, and immunization of hypercholesterolemic mice against a peptide derived from TCR TRBV31 inhibited the development of atherosclerosis.

These results strongly suggest that autoimmune T cells recognizing protein epitopes from native LDL promote atherosclerosis.

In summary, in several embodiments, T cell responses against modified LDL were investigated by immunizing mice with oxLDL. T cell hybridomas were established from such mice and analyzed for their reactivity towards oxidized and native forms of LDL. None of the reactive clones responded to oxidized LDL but only to native LDL and purified apolipoprotein B-100. Responding hybridomas were CD3+4+8−, restricted by MHC class II antigen I-Ab, and expressed one single T cell receptor variable (V) beta chain (TRBV31) in combination with different V alpha chains. Immunization of huApoB100$^{tg}$×Ldlr$^{-/-}$ mice against TRBV31 reduced atherosclerosis, in parallel with the development of anti-TRBV3 antibodies that blocked T cell recognition of ApoB100.

The examples set forth above are provided to give those of ordinary skill in the art a complete disclosure and description of how to make and use the embodiments of the compositions, peptides, proteins, methods and systems of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular fowls "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Although any methods and materials similar or equivalent to those described herein can be used in the practice for testing of the products, methods and system of the present disclosure, exemplary appropriate materials and methods are described herein as examples and for guidance purpose.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A method to treat atherosclerosis in an individual, the method comprising:
administering a therapeutically effective amount of a compound inhibiting in the individual a CD4$^+$ T cell response to ApoB100, wherein the compound comprises T cell receptor beta variable 31 (TCR TRBV31) or T cell receptor beta variable 30 (TCR TRBV30), or an immunogenic fragment thereof; or an antibody reactive to TRBV31 or TRBV30 or an immunogenic fragment thereof; and wherein administration of the compound treats atherosclerosis in the individual.

2. The method of claim 1, wherein the compound inhibiting the CD4$^+$ T cell response to ApoB100 is a compound that has been identified to have a capacity to prevent activation of a hybridoma clone 48-5 upon exposure to ApoB100 or a fragment thereof, wherein the hybridoma clone 48-5 is the hybridoma clone that has been deposited according to the Budapest Treaty with the DSMZ-Deutsche Sammlung von Mikro-organismen and Zellkulturen GmbH, lnhoffenstrasse 7 B, 38124 Braunschweig, Germany, on Jan. 22, 2009 with the accession number DSM ACC2986.

3. The method of claim 1 wherein the CD4$^+$ T cell is a CD4$^+$ T cell presenting a T cell receptor beta variable 31 (TCR TRBV31).

4. The method of claim 1, wherein the CD4$^+$ T cell is a T helper cell.

5. The method of claim 1, wherein the inhibiting is performed by inhibiting the binding of TRBV31 to ApoB100 or a fragment thereof.

6. A method to treat atherosclerosis in an individual, the method comprising:
immunizing the individual against T cell receptor beta variable 31 (TRBV31) or T cell receptor beta variable 30 (TRBV30), wherein the immunizing is performed by administering T cell receptor beta variable 31 (TCR TRBV31) or T cell receptor beta variable 30 (TCR TRBV30) or an immunogenic fragment thereof, and wherein the administration treats atherosclerosis in the individual.

7. The method of claim 6, wherein the immunizing is performed by administering an immunogenic fragment of CDR2 variable region of TCR TRBV31.

8. The method of claim 6, wherein the immunizing is performed by administering a peptide having the sequence of SEQ ID NO:1 or an immunogenic fragment thereof.

9. The method of claim 6, wherein the immunizing is performed by administering an immunogenic fragment of CDR2 variable region of TCR TRBV30.

* * * * *

SEQUENCE LISTING

```
<160> NUMBER OF SEQ ID NOS: 54

<210> SEQ ID NO 1
<211> LENGTH: 18
<212> TYPE: PRT
<213> ORGANISM: Mus musculus

<400> SEQUENCE: 1

Ala Thr Gly Gly Thr Leu Gln Gln Leu Phe Tyr Ser Ile Thr Val Gly
1               5                   10                  15

Gln Val

<210> SEQ ID NO 2
<211> LENGTH: 21
<212> TYPE: DNA
<213> ORGANISM: Unknown
<220> FEATURE:
<223> OTHER INFORMATION: primer

<400> SEQUENCE: 2
tggatggttt gaaggacagt g                                             21

<210> SEQ ID NO 3
<211> LENGTH: 21
<212> TYPE: DNA
<213> ORGANISM: Unknown
<220> FEATURE:
<223> OTHER INFORMATION: primer

<400> SEQUENCE: 3
ctgtttatct ctgctgaccg g                                             21

<210> SEQ ID NO 4
<211> LENGTH: 22
<212> TYPE: DNA
<213> ORGANISM: Unknown
<220> FEATURE:
<223> OTHER INFORMATION: primer

<400> SEQUENCE: 4
acgaaggaca aggattcact gt                                            22

<210> SEQ ID NO 5
<211> LENGTH: 22
<212> TYPE: DNA
<213> ORGANISM: Unknown
<220> FEATURE:
<223> OTHER INFORMATION: primer

<400> SEQUENCE: 5
```

```
ctggaggact caggcactta ct                                              22

<210> SEQ ID NO 6
<211> LENGTH: 21
<212> TYPE: DNA
<213> ORGANISM: Unknown
<220> FEATURE:
<223> OTHER INFORMATION: primer

<400> SEQUENCE: 6
ggtacccgac tcttttctgg t                                               21

<210> SEQ ID NO 7
<211> LENGTH: 22
<212> TYPE: DNA
<213> ORGANISM: Unknown
<220> FEATURE:
<223> OTHER INFORMATION: primer

<400> SEQUENCE: 7 acccttcag aagatgactt cc                                               22

<210> SEQ ID NO 8
<211> LENGTH: 20
<212> TYPE: DNA
<213> ORGANISM: Unknown
<220> FEATURE:
<223> OTHER INFORMATION: primer

<400> SEQUENCE: 8
tttaaagtcc caaaggccaa                                                 20

<210> SEQ ID NO 9
<211> LENGTH: 21
<212> TYPE: DNA
<213> ORGANISM: Unknown
<220> FEATURE:
<223> OTHER INFORMATION: primer

<400> SEQUENCE: 9
tcctgaaagt cattacggct g                                               21

<210> SEQ ID NO 10
<211> LENGTH: 21
<212> TYPE: DNA
<213> ORGANISM: Unknown
<220> FEATURE:
<223> OTHER INFORMATION: primer

<400> SEQUENCE: 10
agagcctcaa gggacaaaga g                                               21

<210> SEQ ID NO 11
<211> LENGTH: 20
<212> TYPE: DNA
<213> ORGANISM: Unknown
<220> FEATURE:
<223> OTHER INFORMATION: primer

<400> SEQUENCE: 11
agactcccag cccagtgact                                                 20

<210> SEQ ID NO 12
<211> LENGTH: 19
<212> TYPE: DNA
<213> ORGANISM: Unknown
<220> FEATURE:
```

<223> OTHER INFORMATION: primer

<400> SEQUENCE: 12
acatcagaga gccgcaacc                                            19

<210> SEQ ID NO 13
<211> LENGTH: 21
<212> TYPE: DNA
<213> ORGANISM: Unknown
<220> FEATURE:
<223> OTHER INFORMATION: primer

<400> SEQUENCE: 13
ccctgcccag ctaatcttaa t                                         21

<210> SEQ ID NO 14
<211> LENGTH: 22
<212> TYPE: DNA
<213> ORGANISM: Unknown
<220> FEATURE:
<223> OTHER INFORMATION: primer

<400> SEQUENCE: 14
ctgcagctga gatgcaagta tt                                        22

<210> SEQ ID NO 15
<211> LENGTH: 22
<212> TYPE: DNA
<213> ORGANISM: Unknown
<220> FEATURE:
<223> OTHER INFORMATION: primer

<400> SEQUENCE: 15
tcctatggtg gatccattta cc                                        22

<210> SEQ ID NO 16
<211> LENGTH: 20
<212> TYPE: DNA
<213> ORGANISM: Unknown
<220> FEATURE:
<223> OTHER INFORMATION: primer

<400> SEQUENCE: 16
tggacagaaa acagagccaa                                           20

<210> SEQ ID NO 17
<211> LENGTH: 20
<212> TYPE: DNA
<213> ORGANISM: Unknown
<220> FEATURE:
<223> OTHER INFORMATION: primer

<400> SEQUENCE: 17
caggcaaagg tcttgtgtcc                                           20

<210> SEQ ID NO 18
<211> LENGTH: 21
<212> TYPE: DNA
<213> ORGANISM: Unknown
<220> FEATURE:
<223> OTHER INFORMATION: primer

<400> SEQUENCE: 18
acgccactct ccataagagc a                                         21

<210> SEQ ID NO 19

```
<211> LENGTH: 20
<212> TYPE: DNA
<213> ORGANISM: Unknown
<220> FEATURE:
<223> OTHER INFORMATION: primer

<400> SEQUENCE: 19
gctctttgca catttcctcc                                              20

<210> SEQ ID NO 20
<211> LENGTH: 22
<212> TYPE: DNA
<213> ORGANISM: Unknown
<220> FEATURE:
<223> OTHER INFORMATION: primer

<400> SEQUENCE: 20
tgcagttatg aggacagcac tt                                           22

<210> SEQ ID NO 21
<211> LENGTH: 23
<212> TYPE: DNA
<213> ORGANISM: Unknown
<220> FEATURE:
<223> OTHER INFORMATION: primer

<400> SEQUENCE: 21
ctgcagttat gagaacagtg ctt                                          23

<210> SEQ ID NO 22
<211> LENGTH: 20
<212> TYPE: DNA
<213> ORGANISM: Unknown
<220> FEATURE:
<223> OTHER INFORMATION: primer

<400> SEQUENCE: 22
ccagacgatt cgggaaagta                                              20

<210> SEQ ID NO 23
<211> LENGTH: 21
<212> TYPE: DNA
<213> ORGANISM: Unknown
<220> FEATURE:
<223> OTHER INFORMATION: primer

<400> SEQUENCE: 23
ttccatcgga ctcatcatca c                                            21

<210> SEQ ID NO 24
<211> LENGTH: 20
<212> TYPE: DNA
<213> ORGANISM: Unknown
<220> FEATURE:
<223> OTHER INFORMATION: primer

<400> SEQUENCE: 24
aacctgaaga aatccccagc                                              20

<210> SEQ ID NO 25
<211> LENGTH: 22
<212> TYPE: DNA
<213> ORGANISM: Unknown
<220> FEATURE:
<223> OTHER INFORMATION: primer

<400> SEQUENCE: 25
```

```
ggaagacgga agattcacag tt                                              22

<210> SEQ ID NO 26
<211> LENGTH: 22
<212> TYPE: DNA
<213> ORGANISM: Unknown
<220> FEATURE:
<223> OTHER INFORMATION: primer

<400> SEQUENCE: 26
acgctcctaa tagacattcg ct                                              22

<210> SEQ ID NO 27
<211> LENGTH: 20
<212> TYPE: DNA
<213> ORGANISM: Unknown
<220> FEATURE:
<223> OTHER INFORMATION: primer

<400> SEQUENCE: 27
gttcctcttc agggtccaga                                                 20

<210> SEQ ID NO 28
<211> LENGTH: 20
<212> TYPE: DNA
<213> ORGANISM: Unknown
<220> FEATURE:
<223> OTHER INFORMATION: primer

<400> SEQUENCE: 28
caccagcagg ttctgggttc                                                 20

<210> SEQ ID NO 29
<211> LENGTH: 20
<212> TYPE: DNA
<213> ORGANISM: Unknown
<220> FEATURE:
<223> OTHER INFORMATION: primer

<400> SEQUENCE: 29
acacgggtca ctgatacgga                                                 20

<210> SEQ ID NO 30
<211> LENGTH: 21
<212> TYPE: DNA
<213> ORGANISM: Unknown
<220> FEATURE:
<223> OTHER INFORMATION: primer

<400> SEQUENCE: 30
atggacaatc agactgcctc a                                               21

<210> SEQ ID NO 31
<211> LENGTH: 21
<212> TYPE: DNA
<213> ORGANISM: Unknown
<220> FEATURE:
<223> OTHER INFORMATION: primer

<400> SEQUENCE: 31
tcactctgaa aatccaaccc a                                               21

<210> SEQ ID NO 32
<211> LENGTH: 21
<212> TYPE: DNA
<213> ORGANISM: Unknown
<220> FEATURE:
```

<223> OTHER INFORMATION: primer

<400> SEQUENCE: 32
taaacgaaac agttccaagg c                                          21

<210> SEQ ID NO 33
<211> LENGTH: 20
<212> TYPE: DNA
<213> ORGANISM: Unknown
<220> FEATURE:
<223> OTHER INFORMATION: primer

<400> SEQUENCE: 33
acggtgccca gtcgttttat                                            20

<210> SEQ ID NO 34
<211> LENGTH: 21
<212> TYPE: DNA
<213> ORGANISM: Unknown
<220> FEATURE:
<223> OTHER INFORMATION: primer

<400> SEQUENCE: 34
ggattcctac ccagcagatt c                                          21

<210> SEQ ID NO 35
<211> LENGTH: 21
<212> TYPE: DNA
<213> ORGANISM: Unknown
<220> FEATURE:
<223> OTHER INFORMATION: primer

<400> SEQUENCE: 35
agataaagga aacctgccca g                                          21

<210> SEQ ID NO 36
<211> LENGTH: 21
<212> TYPE: DNA
<213> ORGANISM: Unknown
<220> FEATURE:
<223> OTHER INFORMATION: primer

<400> SEQUENCE: 36
ccagaacaac gcaagaagac t                                          21

<210> SEQ ID NO 37
<211> LENGTH: 20
<212> TYPE: DNA
<213> ORGANISM: Unknown
<220> FEATURE:
<223> OTHER INFORMATION: primer

<400> SEQUENCE: 37
ggctaccccc tctcagacat                                            20

<210> SEQ ID NO 38
<211> LENGTH: 20
<212> TYPE: DNA
<213> ORGANISM: Unknown
<220> FEATURE:
<223> OTHER INFORMATION: primer

<400> SEQUENCE: 38
tggcttccct ttctcagaca                                            20

<210> SEQ ID NO 39

```
<211> LENGTH: 20
<212> TYPE: DNA
<213> ORGANISM: Unknown
<220> FEATURE:
<223> OTHER INFORMATION: primer

<400> SEQUENCE: 39
gcgacacagc cacctatctc                                              20

<210> SEQ ID NO 40
<211> LENGTH: 21
<212> TYPE: DNA
<213> ORGANISM: Unknown
<220> FEATURE:
<223> OTHER INFORMATION: primer

<400> SEQUENCE: 40
cgcagcaagt ctcttatgga a                                            21

<210> SEQ ID NO 41
<211> LENGTH: 21
<212> TYPE: DNA
<213> ORGANISM: Unknown
<220> FEATURE:
<223> OTHER INFORMATION: primer

<400> SEQUENCE: 41
atagatgatt cagggatgcc c                                            21

<210> SEQ ID NO 42
<211> LENGTH: 21
<212> TYPE: DNA
<213> ORGANISM: Unknown
<220> FEATURE:
<223> OTHER INFORMATION: primer

<400> SEQUENCE: 42
tgagaagttc caatccagtc g                                            21

<210> SEQ ID NO 43
<211> LENGTH: 20
<212> TYPE: DNA
<213> ORGANISM: Unknown
<220> FEATURE:
<223> OTHER INFORMATION: primer

<400> SEQUENCE: 43
gaaggctatg atgcgtctcg                                              20

<210> SEQ ID NO 44
<211> LENGTH: 20
<212> TYPE: DNA
<213> ORGANISM: Unknown
<220> FEATURE:
<223> OTHER INFORMATION: primer

<400> SEQUENCE: 44
ttcccatcag tcatcccaac                                              20

<210> SEQ ID NO 45
<211> LENGTH: 21
<212> TYPE: DNA
<213> ORGANISM: Unknown
<220> FEATURE:
<223> OTHER INFORMATION: primer

<400> SEQUENCE: 45
```

```
aaaatgccct gctaagaaac c                                              21

<210> SEQ ID NO 46
<211> LENGTH: 19
<212> TYPE: DNA
<213> ORGANISM: Unknown
<220> FEATURE:
<223> OTHER INFORMATION: primer

<400> SEQUENCE: 46
cagcctggga atcagaacg                                                 19

<210> SEQ ID NO 47
<211> LENGTH: 21
<212> TYPE: DNA
<213> ORGANISM: Unknown
<220> FEATURE:
<223> OTHER INFORMATION: primer

<400> SEQUENCE: 47
gcatcctgga aatcctatcc t                                              21

<210> SEQ ID NO 48
<211> LENGTH: 21
<212> TYPE: DNA
<213> ORGANISM: Unknown
<220> FEATURE:
<223> OTHER INFORMATION: primer

<400> SEQUENCE: 48
agtgtccttc aaactcacct t                                              21

<210> SEQ ID NO 49
<211> LENGTH: 21
<212> TYPE: DNA
<213> ORGANISM: Unknown
<220> FEATURE:
<223> OTHER INFORMATION: primer

<400> SEQUENCE: 49
aaaggataca gggtctcacg g                                              21

<210> SEQ ID NO 50
<211> LENGTH: 21
<212> TYPE: DNA
<213> ORGANISM: Unknown
<220> FEATURE:
<223> OTHER INFORMATION: primer

<400> SEQUENCE: 50
ggacaagttt ccaatcagcc g                                              21

<210> SEQ ID NO 51
<211> LENGTH: 21
<212> TYPE: DNA
<213> ORGANISM: Unknown
<220> FEATURE:
<223> OTHER INFORMATION: primer

<400> SEQUENCE: 51
ttcatcctaa gcacggagaa g                                              21

<210> SEQ ID NO 52
<211> LENGTH: 24
<212> TYPE: DNA
<213> ORGANISM: Unknown
<220> FEATURE:
```

```
<223> OTHER INFORMATION: primer

<400> SEQUENCE: 52
tgcaatctct gcttttgatg gctc                                          24

<210> SEQ ID NO 53
<211> LENGTH: 14
<212> TYPE: DNA
<213> ORGANISM: Unknown
<220> FEATURE:
<223> OTHER INFORMATION: primer

<400> SEQUENCE: 53
tccacccaag gtct                                                     14

<210> SEQ ID NO 54
<211> LENGTH: 14
<212> TYPE: DNA
<213> ORGANISM: Unknown
<220> FEATURE:
<223> OTHER INFORMATION: primer

<400> SEQUENCE: 54
tccacccaag gtct                                                     14
```